(12) United States Patent
Sakaguchi et al.

(10) Patent No.: US 7,496,175 B2
(45) Date of Patent: Feb. 24, 2009

(54) X-RAY DIAGNOSTIC APPARATUS AND IMAGE PROCESSING APPARATUS

(75) Inventors: Takuya Sakaguchi, Shioya-gun (JP); Takashi Ichihara, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/830,252

(22) Filed: Jul. 30, 2007

(65) Prior Publication Data

US 2008/0107233 A1 May 8, 2008

(30) Foreign Application Priority Data

| Nov. 8, 2006 | (JP) | ............................. 2006-302994 |
| Nov. 10, 2006 | (JP) | ............................. 2006-305878 |
| Dec. 27, 2006 | (JP) | ............................. 2006-353430 |

(51) Int. Cl.
  *H05G 1/10* (2006.01)
(52) U.S. Cl. ........................... 378/95; 600/428; 600/431
(58) Field of Classification Search ..................... 378/8, 378/91, 95, 101, 109, 110, 111, 112, 193–198; 600/425, 428, 431
  See application file for complete search history.

(56) References Cited

U.S. PATENT DOCUMENTS

| 4,185,198 A | 1/1980 | Fujimoto ................... 378/98.5 |
| 4,611,340 A | 9/1986 | Okazaki ....................... 378/95 |
| 4,709,332 A | 11/1987 | Morrison et al. ............ 600/431 |

FOREIGN PATENT DOCUMENTS

| DE | 42 10 121 C1 | 4/1993 |
| DE | 10 2005 018 327 A1 | 10/2006 |
| GB | 2 107 553 A | 4/1983 |
| GB | 2 357 953 A | 7/2001 |
| WO | WO 02/083001 A1 | 10/2002 |

OTHER PUBLICATIONS

C. Michael Gibson, MS, MD, et al., "Relationship of TIMI Myocardial Perfusion Grade to Mortality After Administration of Thrombolytic Drugs", Clinical Investigation and Reports, Circulation, 101, Jan. 18, 2000, pp. 125-130.

Arnoud W. J. van 't Hof, MD, et al., "Angiographic Assessment of Myocardial Reperfusion in Patients Treated With Primary Angioplasty for Acute Myocardial Infarction. Myocardial Blush Grade", Clinical Investigation and Reports, Jun. 16, 1998, pp. 2302-2306.

*Primary Examiner*—Courtney Thomas
(74) *Attorney, Agent, or Firm*—Oblon, Spivak, McClelland, Maier & Neustadt, P.C.

(57) ABSTRACT

An image processing apparatus includes a storage unit which stores the data of a plurality of images in an angiography sequence, and a computation unit which generates a reference time density curve concerning a reference region set in a blood supply region to a blood supplied region and a plurality of time density curves concerning a plurality of local regions set in the blood supplied region on the basis of the data of a plurality of images, and computes a plurality of indexes respectively representing the correlations of the plurality of time density curves with respect to the reference time density curve.

37 Claims, 26 Drawing Sheets

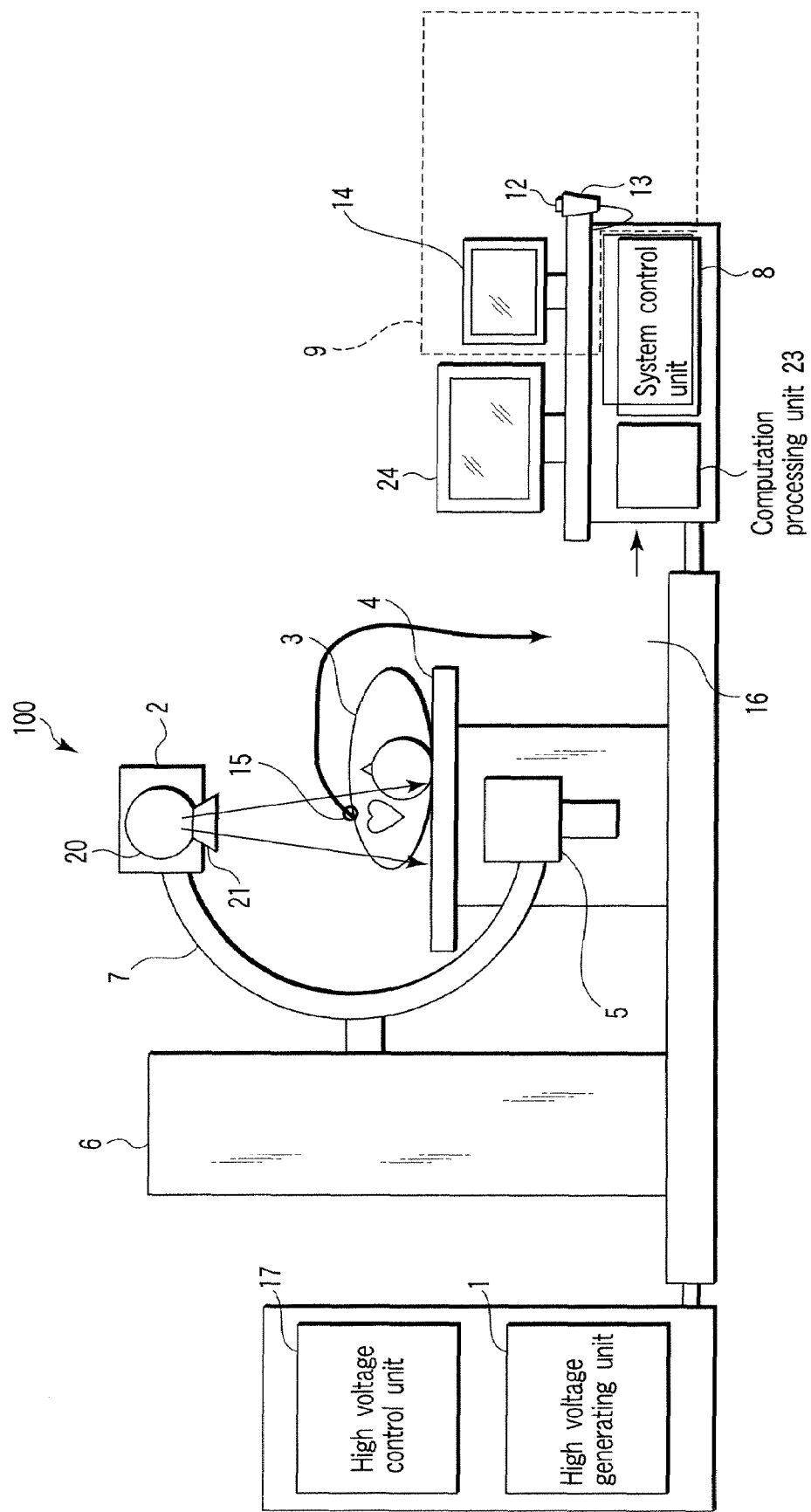
F I G. 10

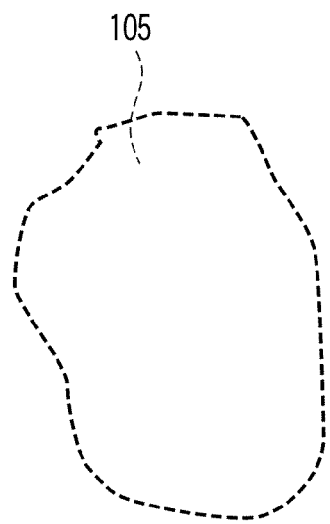
F I G. 15A
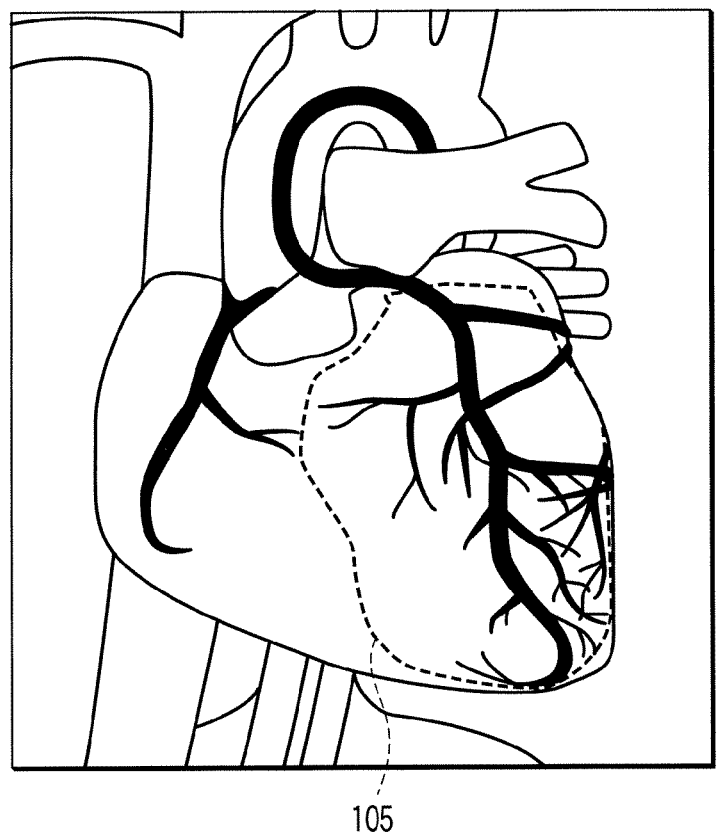
F I G. 15B $Y(t) = \int_0^t C_{myo}(\tau)d\tau / \int_0^t C_a(\tau)d\tau$
$Y(t) = C_{myo}(t) / \int_0^t C_a(\tau)d\tau$

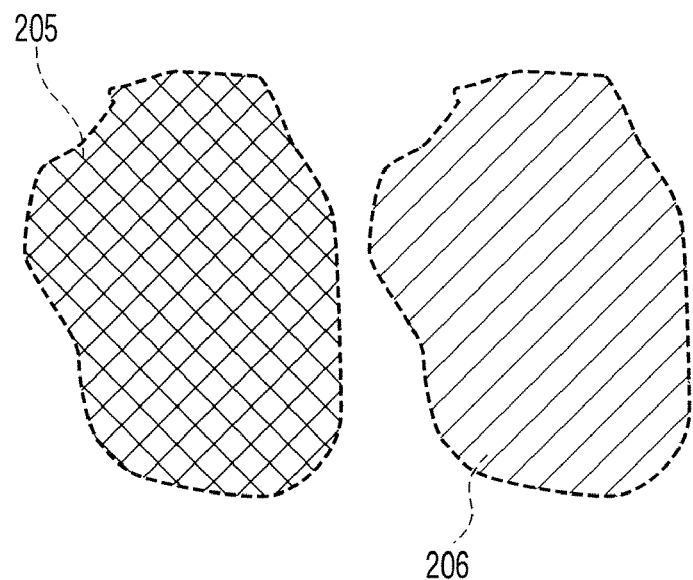
F I G. 20A
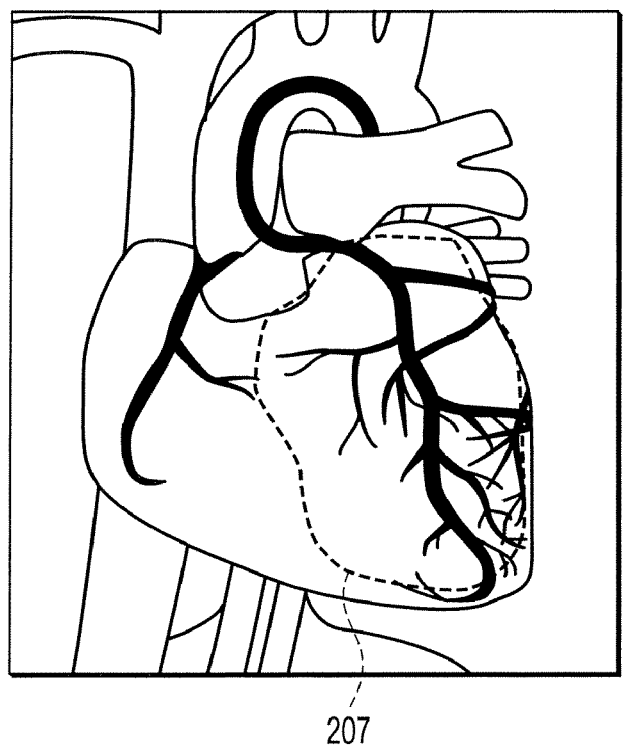
F I G. 20B

| | Visual classification according to reference by Gibson | Method according to this embodiment |
|---|---|---|
| TMP Grade 0 | Failure of dye to enter the microvasculature. Either minimal or no ground-glass appearance ("blush") or opacification of the myocardium in the distribution of the culprit artery, indicating lack of tissue-level perfusion | $K_1 \cong 0$ |
| TMP Grade 1 | Dye slowly enters but fails to exit the microvasculature. There is the ground-glass appearance ("blush") or opacification of the myocardium in the distribution of the culprit lesion that fails to clear from the microvasculature, and dye staining is present on the next injection (~30 seconds between injections). | $K_1$ is less than predetermined threshold $K_2 \cong 0$ |
| TMP Grade 2 | Delayed entry and exit of dye from the microvasculature. There is the ground-glass appearance ("blush") or opacification of the myocardium in the distribution of the culprit lesion that is strongly persistent at the end of the washout phase (ie, dye is strongly persistent after 3 cardiac cycles of the washout phase and either does not or only minimally diminishes in intensity during washout). | $K_1$ and $K_2$ are less than predetermined threshold |
| TMP Grade 3 | Normal entry and exit of dye from the microvasculature. There is the ground-glass appearance ("blush") or opacification of the myocardium in the distribution of the culprit lesion that clears normally and is either gone or only mildly/moderately persistent at the end of the washout phase (ie, dye is gone or is mildly/moderately persistent after 3 cardiac cycles of the washout phase and noticeably diminishes in intensity during the washout phase), similar to that in an uninvolved artery. | Both $K_1$ and $K_2$ are more than predetermined threshold |

F I G. 28

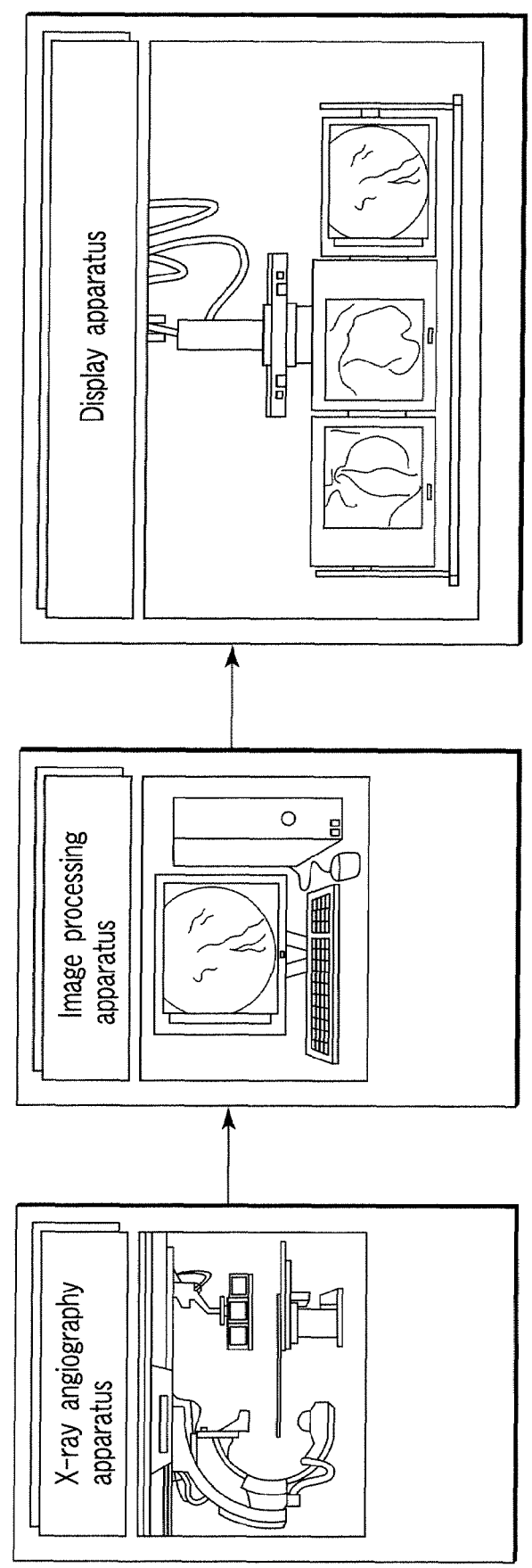
F I G. 30

X-RAY DIAGNOSTIC APPARATUS AND IMAGE PROCESSING APPARATUS

CROSS-REFERENCE TO RELATED APPLICATIONS

This application is based upon and claims the benefit of priority from prior Japanese Patent Applications No. 2006-302994, filed Nov. 8, 2006; No. 2006-305878, filed Nov. 10, 2006; and No. 2006-353430, filed Dec. 27, 2006, the entire contents of all of which are incorporated herein by reference.

BACKGROUND OF THE INVENTION

1. Field of the Invention

The present invention relates to an X-ray diagnostic apparatus which radiographs a subject to be examined by using pulse X-rays and an image processing apparatus suitable for coronary angiographic diagnosis using X-rays.

2. Description of the Related Art

There is available a method of performing angiography after an intravascular intervention treatment, observing a temporal change in the manner of the flow of a contrast medium into the cardiac muscle, and supporting the determination of the end of the treatment. Since the release of the article (by Gibson) in 2000 which stated that this method allowed to predict a prognosis, the method has often been used to evaluate beneficial effects and manipulations/techniques.

Although it has been evident that the index based on this method is clinically useful, the index has not been used in daily routine clinical practices. This is because the method increases radiation exposure and is low in quantitativeness.

A radiography whose examination purpose is blood vessel morphology observation generally performs radiography in the manner shown in FIG. 6. That is, this method obtains an image by applying X-rays for a period of three to five heartbeats in terms of cardiac motion or about five sec in terms of a radiography time.

If the examination purpose of this method is to measure myocardial perfusion, it is necessary to perform radiography for a long period of time. It is thought that continuous observation for at least five sec, or about 30 sec in general, or about 60 sec at most is preferable. For this reason, if this radiography whose purpose is myocardial perfusion is to be performed in addition to radiography whose purpose is to perform blood vessel morphology observation, it is necessary to perform radiography like that shown in FIG. 7.

It is conceivable to provide another proposal of separately performing radiography whose purpose is blood vessel morphology observation and radiography whose purpose is myocardial perfusion, i.e., a total of two radiographic cycles. In this case, however, the amount of contrast medium injected doubles. This is most undesirable.

In addition, a conventional X-ray diagnostic apparatus for blood vessel observation, i.e., a so-called X-ray angiography apparatus, performs coronary angiography, but cannot quantitatively measure a myocardial blood flow by using a contrast medium. It is therefore necessary to measure a myocardial blood flow in another room or in another time zone by using a nuclear medicine diagnosis apparatus or MRI apparatus.

Assume that there are a plurality of stenoses in a coronary artery. Currently no method is available in cathether room to determine which of plurality of stenosis is major reason of ischemia. When interventional treatment has been done for, embolus, or thrombus in a peripheral vessel of a coronary artery, it is difficult to verify that enough blood is now supplied to cardiac muscle so that treatment can be finished at this time, Note that the following two references (a) and (b) are related arts:

(a) Relationship of TIMI Myocardial Perfusion Grade to Mortality After Administration of Thrombolytic Drugs, C. Michael Gibson, MS, MD; Christopher P. Cannon, MD; Sabina A. Murphy, MPH; Kathryn A. Ryan, BS; Rebecca Mesley, BS; Susan J. Marble, RN, MS; Carolyn H. McCabe, BS; Frans Van de Werf, MD, PhD; Eugene Braunwald, MD;, Circulation, 101, 125-130, 2000

(b) Arnoud W. J. van't Hof, MD; Aylee Liem, MD; Harry Suryapranata, MD; Jan C. A. Hoorntje, MD; Menko-Jan de Boer, MD; Felix Zijlstra, MD;, Angiographic Assessment of Myocardial Reperfusion in Patients Treated With Primary Angioplasty for Acute Myocardial Infarction, Myocardial Blush Grade, Circulation, 97, 2302-2306, 1998)

BRIEF SUMMARY OF THE INVENTION

It is an object of the present invention to achieve reductions in radiation exposure and the amount of contrast medium injected in radiography with, for example, both purposes of blood vessel morphology observation and myocardial perfusion, which require a relatively long radiography time.

It is another object of the present invention to provide useful information concerning a myocardial blood flow.

Additional objects and advantages of the present invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the present invention, and together with the general description given above and the detailed description of the embodiments given below, serve to explain the principles of the invention.

FIG. 10 is a view showing the arrangement of an X-ray diagnostic apparatus according to the second embodiment of the present invention;

FIG. 15A is a view showing a perfusion computation range in this embodiment;

FIG. 15B is a view showing a perfusion computation range set on a CAG image in this embodiment;

FIG. 20A is a view showing perfusion computation ranges at rest and under stress in this embodiment;

FIG. 20B is a view showing a comparison image between images at rest and under stress which are generated by the image processing unit in FIG. 2;

FIG. 28 is a view showing a classification table for classification of local regions by the image processing unit in FIG. 11 using two types of indexes;

FIG. 30 is a view showing an image processing apparatus independent of an X-ray diagnostic apparatus in this embodiment;

DETAILED DESCRIPTION OF THE INVENTION

First Embodiment

The first embodiment of the present invention will be described below with reference to the views of the accompanying drawing.

The terms used in the following description will be defined as follows:

pulse rate: an index which specifies the frequency of applying pulse X-rays to a subject, and a value expressing the number of times of application of pulse X-rays per unit time (per sec or min) or heartbeat with the unit (times/sec or times/min) or (times/heartbeat). A frame rate representing the number of images radiographed per unit time is almost equivalent to a pulse rate. Note that the application of pulse X-rays includes not only the form of generating pulse X-rays from an X-ray tube and directly applying them to a subject but also the form of continuously generating X-rays, generating pulse X-rays by using an X-ray shutter or the like, and applying them to a subject.

perfusion: the flow of blood to the cardiac muscle.

R wave: a peak wave of an electrocardiographic waveform.

R-R interval: the time interval between R waves.

mA: a tube current flowing between the electrodes of an X-ray tube and used as an index representing the height of a pulse X-ray.

pulse width: the duration of a pulse X-ray, which is expressed by the unit "msec".

mAs: the tube current time product obtained by multiplying a tube current by a pulse width and used as an index representing the intensity of X-rays.

protocol: a set of parameters which are various kinds of conditions stored altogether.

Blush: a numerical value obtained by Gibson et al. by converting the degree of flow of a contrast medium into the cardiac muscle into a semiquantitative numerical value.

control image: a reference image.

Figure 1:
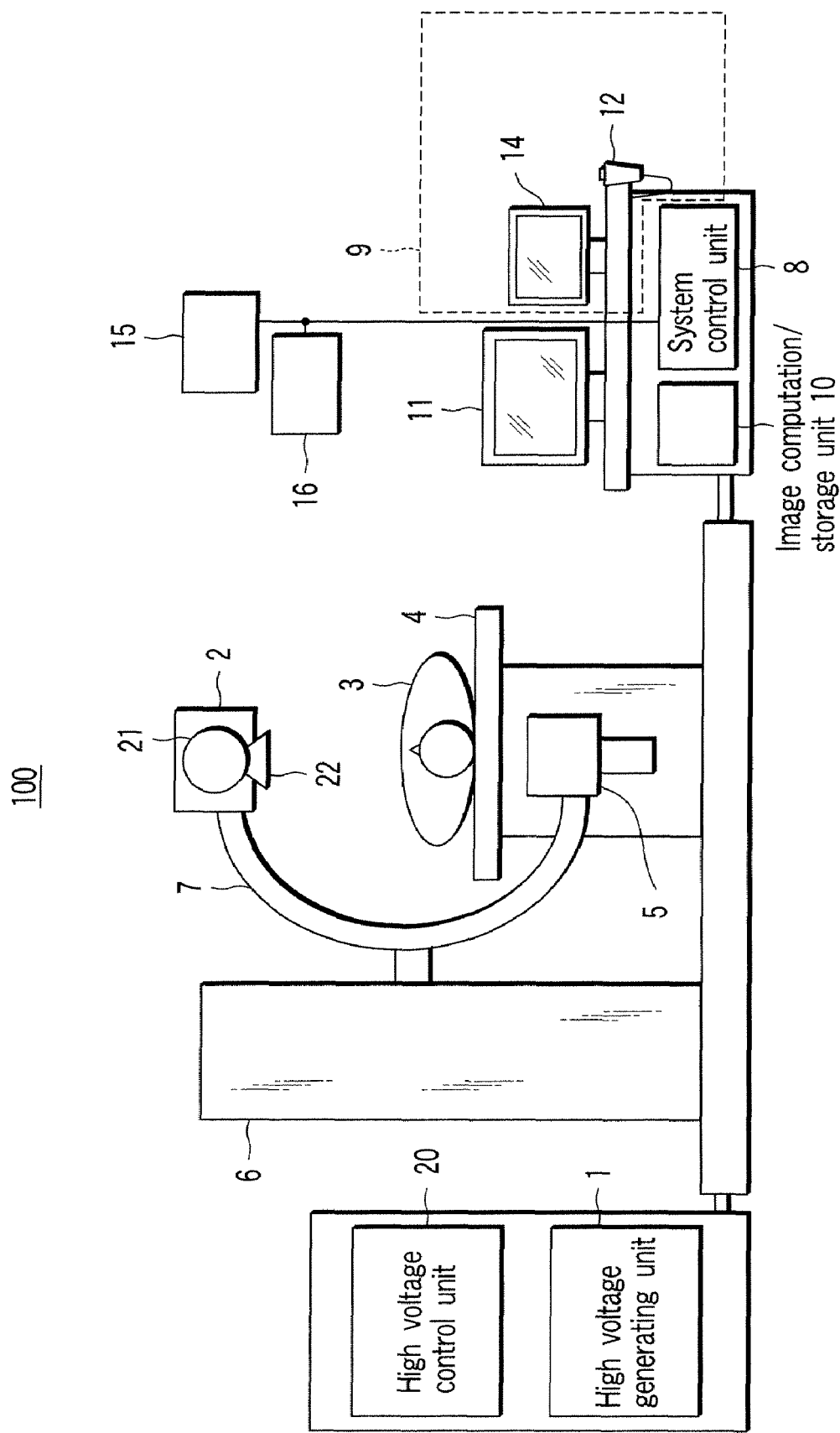
FIG. 1 is a view showing the arrangement of an X-ray diagnostic apparatus according to the first embodiment of the present invention.

FIG. 1 shows an X-ray imaging apparatus according to this embodiment. The X-ray imaging apparatus includes a gantry 100. The gantry 100 includes a C-arm 7. The C-arm 7 is rotatably supported by a support mechanism 6. An X-ray generating unit 2 is mounted on one end of the C-arm 7. The X-ray generating unit 2 includes an X-ray tube 21 and an X-ray collimator 22. A high voltage generating unit 1 generates a high voltage (tube voltage) applied between the electrodes of the X-ray tube 21, and generates a filament current supplied to the filament of the X-ray tube 21. A high voltage control unit 20 controls the tube voltage and/or the filament current generated by the high voltage generating unit 1 under the control of a system control unit 8.

An X-ray detection unit 5 is mounted on the other end of the C-arm 7. The X-ray detection unit 5 faces the X-ray tube 21 of the X-ray generating unit 2 through a subject 3 placed on a bed 4. The X-ray detection unit 5 is typically a solid flat panel detector comprising a two-dimensional array of a plurality of detection elements (pixels) which directly or indirectly convert incident X-rays into electric charges. The X-ray detection unit 5 repeats detecting operation of one cycle typically comprising accumulating electric charges, reading out electric charges, and resetting at a constant cycle under the control of the system control unit 8.

An image computation/storage unit 10 has a function of generating image data on the basis of an output from the X-ray detection unit 5, a function of storing image data, and a function of processing image data. The system control unit 8 has a main function of controlling radiographing operation in the following manner on the basis of an injection start signal output from an injector 15 at the time point when the injector 15 starts injecting a contrast medium into the subject 3, an injection end signal output from the injector 15 at the time point when the injector 15 finishes injecting the contrast medium into the subject, and an electrocardiogram (ECG) of the subject 3 measured by an electrocardiograph 16. An operation unit 9 is connected to the system control unit 8. The operation unit 9 comprises a hand switch 12 and a user interface 14 including a display, a touch panel, and the like.

Figure 2:
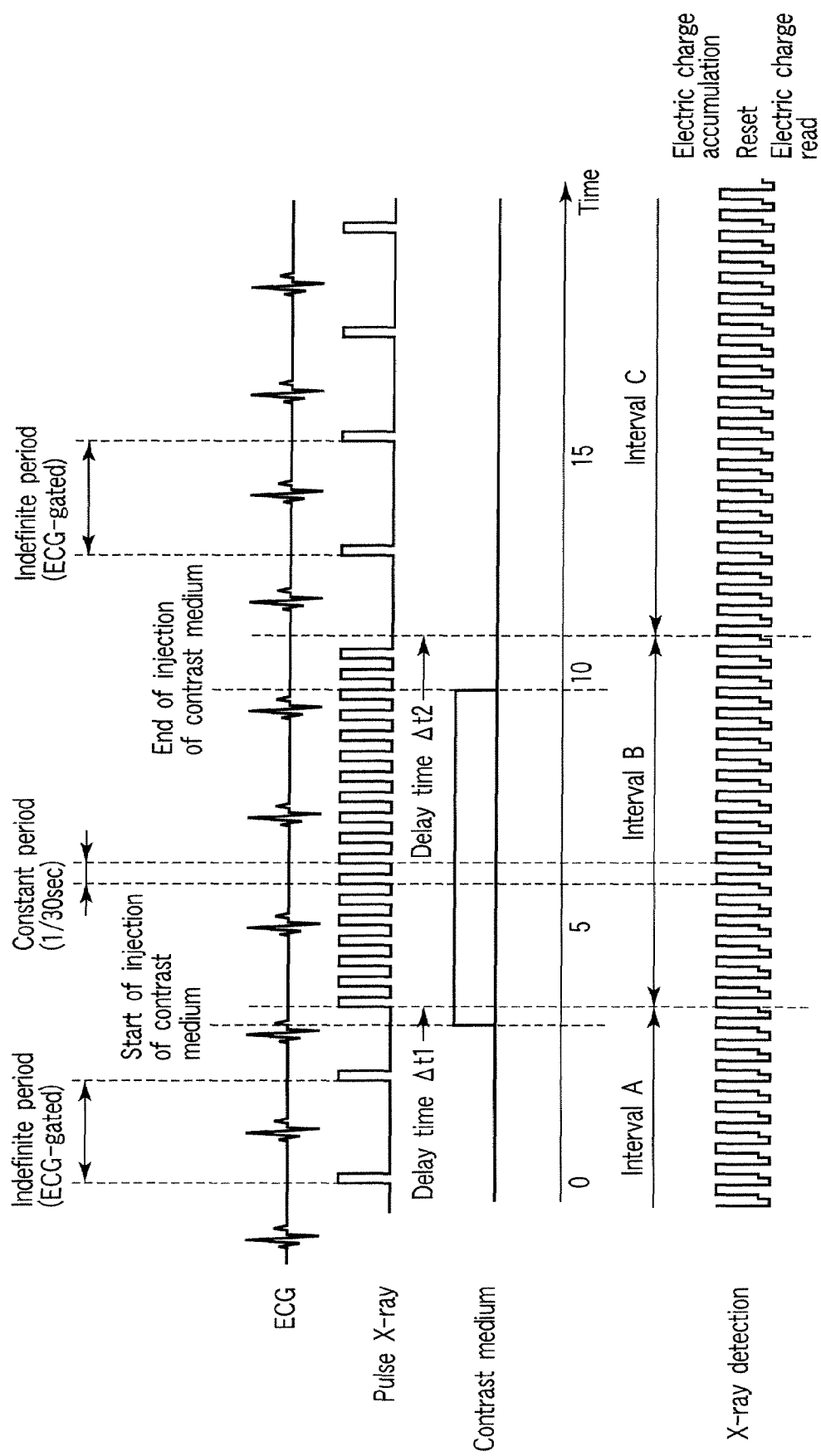
FIG. 2 is a view showing an example of radiographing operation by a system control unit in FIG. 1.

FIG. 2 shows radiographing operation by the system control unit 8. Before radiography, the operator inserts a catheter into a subject up to, for example, the entrance of a coronary artery and starts angiographic examination at this position.

When the examination starts, the generation of pulse X-rays starts. The radiography period from the start of the generation of pulse X-rays to the end of the generation of pulse X-rays can be divided into three intervals (A), (B), and (C) in the order named according to differences in radiography control by the system control unit 8, more specifically, control on the generation of pulse X-rays.

In interval (A), no contrast medium is injected. The time length of this interval corresponds to about one to three heartbeats. In interval (A), pulse X-rays are repeatedly generated at an indefinite cycle in the ECG-gated mode. For example, in interval (A), the system control unit 8 detects R waves of an electrocardiogram (ECG), identifies an end diastole from an R-R interval, and generates pulse X-rays only at this time point. That is, the pulse rate in interval (A) is one time/heartbeat, and pulse X-rays are repeatedly generated at an indefinite cycle.

The X-ray detection unit 5 repeats detecting operation at a constant cycle corresponding to the reciprocal of a frame rate of, e.g., 30 cycles/sec (30 frames per second) in synchronism with clocks throughout the entire radiography period of intervals (A), (B), and (C) including interval (A).

Figure 8:
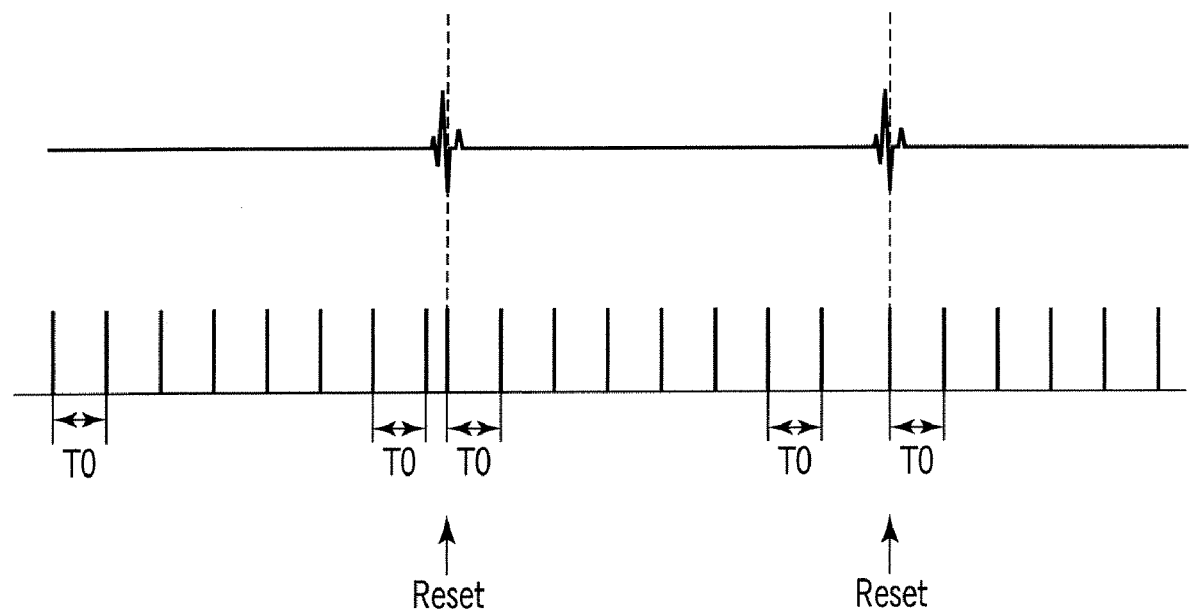
FIG. 8 is a view showing still another radiographing operation by the system control unit in FIG. 1.

It suffices to use a method of acquiring information in the ECG-gated mode at a constant cycle (e.g., the reciprocal of 30 fps). More specifically, as shown in FIG. 8, if, for example, an R wave is detected during the acquisition of information at a constant cycle (e.g., the reciprocal of 30 fps), this method resets the rhythm of application of X-rays at a constant cycle and acquires information at a constant cycle (e.g., the reciprocal of 30 fps) again. According to this technique, a frame immediately after an R wave is ECG-gated at any heartbeat, and information is acquired at a high speed, e.g., at 30 fps, thereafter.

Figure 9:
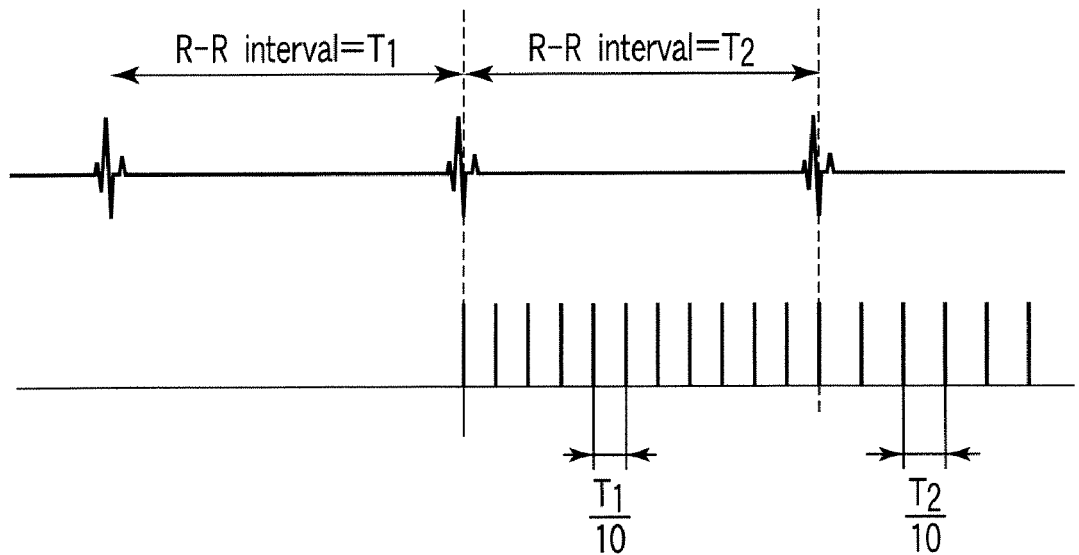
FIG. 9 is a view showing still another radiographing operation by the system control unit in FIG. 1.

In an interval in which information is acquired at a constant cycle (e.g., the reciprocal of 30 fps), as shown in FIG. 9, it suffices to acquire information in the ECG-gated mode at a constant cycle (e.g., 1/10 of an R-R interval). More specifically, as shown in FIG. 9, if, for example, an R wave is detected during the acquisition of information at a constant cycle (e.g., the reciprocal of 30 fps), this method resets the rhythm of application of X-rays at a constant cycle, calculates an R-R interval, and calculates a time corresponding to 1/10 the R-R interval. The method then acquires information at the calculated cycle (constant cycle) in the next heartbeat cycle. According to this technique, a frame immediately after an R wave is ECG-gated at any heartbeat, and information is acquired at a high speed thereafter.

The image computation/storage unit 10 stores image data corresponding to the generation cycle of pulse X-rays. However, the image computation/storage unit 10 does not store image data corresponding to any period at which no pulse X-rays are generated. The image computation/storage unit 10 stores the data of an image together with a code which discriminates interval (A) before the injection of the contrast medium from intervals (B) and (C) to be described later.

The operator triggers the injector 15 to start injecting a contrast medium. The injector 15 supplies a contrast medium injection start signal to the system control unit 8. The system control unit 8 finishes interval (A) after a lapse of a predetermined delay time Δt1 since a contrast medium injection start time point, and starts interval (B). The delay time Δt1 is set to the time required to discharge a contrast medium from the distal end of the catheter from the time point when the injector 15 outputs a contrast medium injection signal, e.g., about one sec.

In interval (B), pulse X-rays are repeatedly generated at a constant cycle. For example, in interval (B), the system control unit 8 repeatedly generates pulse X-rays at a constant cycle corresponding to the reciprocal of the same pulse rate (30 times/sec) as the frame rate of detecting operation, 30 cycles/sec (30 fps), in synchronism with clocks. The time width (duration) of pulse X-rays is set to be equivalent to an electric charge accumulation period length in the detecting operation of the X-ray detection unit 5. As a result, pulse X-rays are generated in synchronism with the detection cycle of the X-ray detection unit 5. In interval (B), image data are generated at a frame rate of 30 fps, and the image computation/storage unit 10 stores all the data. The image acquisition/storage unit 10 stores the data of an image together with a code which discriminates interval (B) during the injection of the contrast medium from intervals (A) and (C) to be described later.

When completing injection of a predetermined amount of contrast medium, the injector 15 supplies a contrast medium injection end signal to the system control unit 8. The system control unit 8 finishes interval (B) after a lapse of a predetermined delay time Δt2 since a contrast medium injection end time point, and starts interval (C). The delay time Δt2 is longer than the delay time t1 and is set to, for example, a time (about two sec) double the time required to discharge a contrast medium from the distal end of the catheter from the time point when the injector 15 outputs a contrast medium injection signal. Interval (B) corresponds to about three to five heartbeats or about five sec.

As in interval (A), in interval (C), pulse X-rays are repeatedly generated at an indefinite cycle in the ECG-gated mode. In interval (C) as well, the system control unit 8 detects R waves of an electrocardiogram (ECG), identifies an end diastole from an R-R interval, and generates pulse X-rays only at this time point. The pulse rate in interval (C) is one time/heartbeat, and pulse X-rays are repeatedly generated at an indefinite cycle. The data of an image is stored together with a code which discriminates interval (C) after the injection of the contrast medium from intervals (A) and (B).

Figure 3:
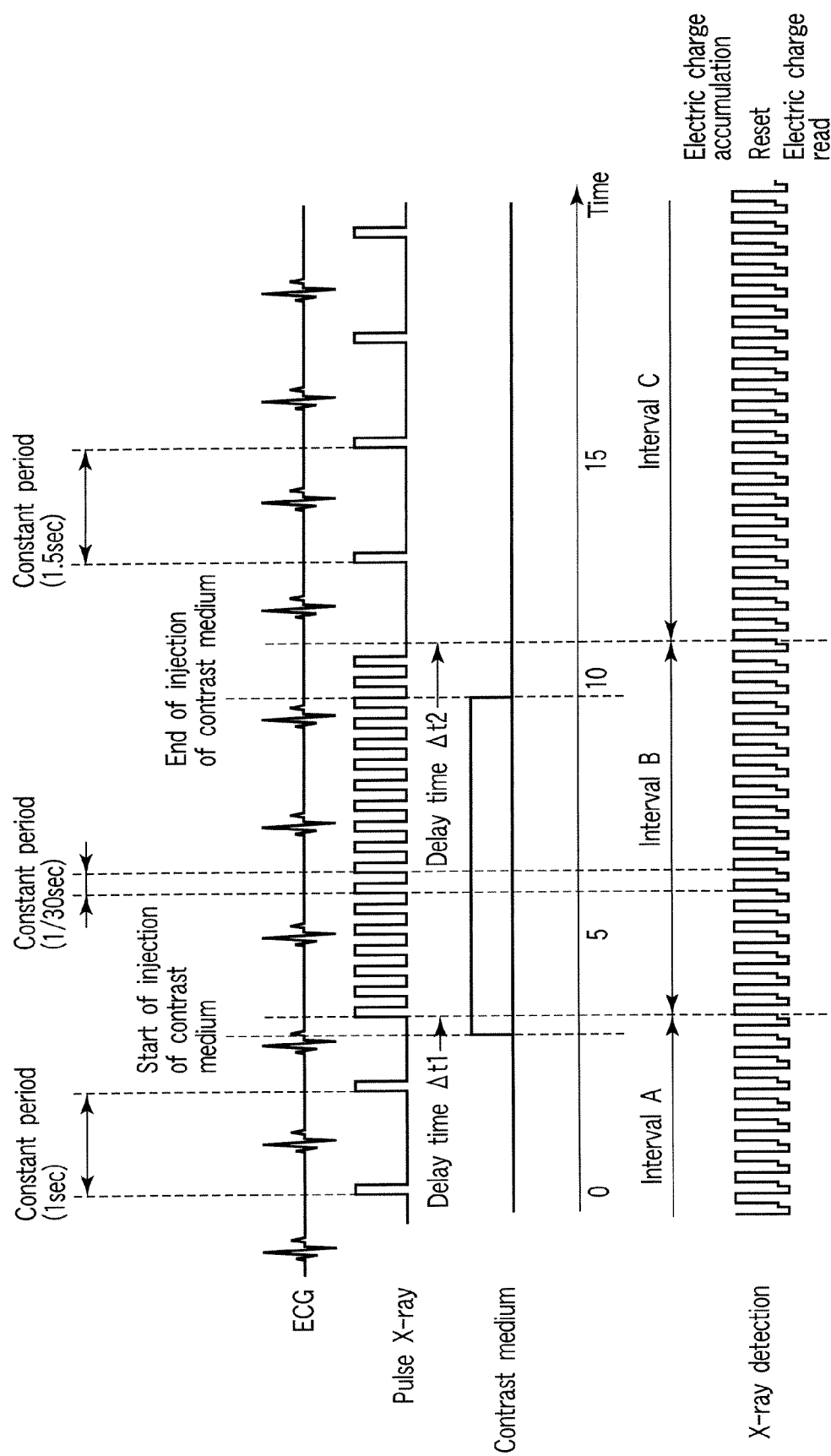
FIG. 3 is a view showing another radiographing operation by the system control unit in FIG. 1.

According to the above description, in intervals (A) and (C), pulse X-rays are generated at an indefinite cycle in the ECG-gated mode. As shown in FIG. 3, however, it suffices to repeatedly generate pulse X-rays at a constant cycle. Typically, in intervals (A) and (C), pulse X-rays are repeatedly generated at a constant cycle (one sec) longer than the cycle (1/30 sec) in interval (B). In this case, the pulse rate in intervals (A) and (C) is 1 time/sec.

The above pulse rate control can reduce the radiation exposure as compared with the case wherein a high pulse rate is kept throughout an entire cycle. In addition, in a period in which a contrast medium flows into a region of interest, a relatively high time resolution can be ensured. In other periods, even with a relatively low time resolution, images at an end diastole which are required for diagnosis can be acquired.

The system control unit 8 determines the end of interval (C) upon receiving an image processing result from the image computation/storage unit 10. For example, the system control unit 8 subtracts a reference image (control image) generated from a plurality of same cardiac phase images acquired in interval (A) from each image acquired in interval (C), and measures the total density of all the obtained differential images or of local regions or the average density (measured value) thereof in real time. The image computation/storage unit 10 generates and stores the above control image as an average image of a plurality of images acquired in interval (A). Performing averaging processing makes it possible to suppress random noise.

Figure 4:
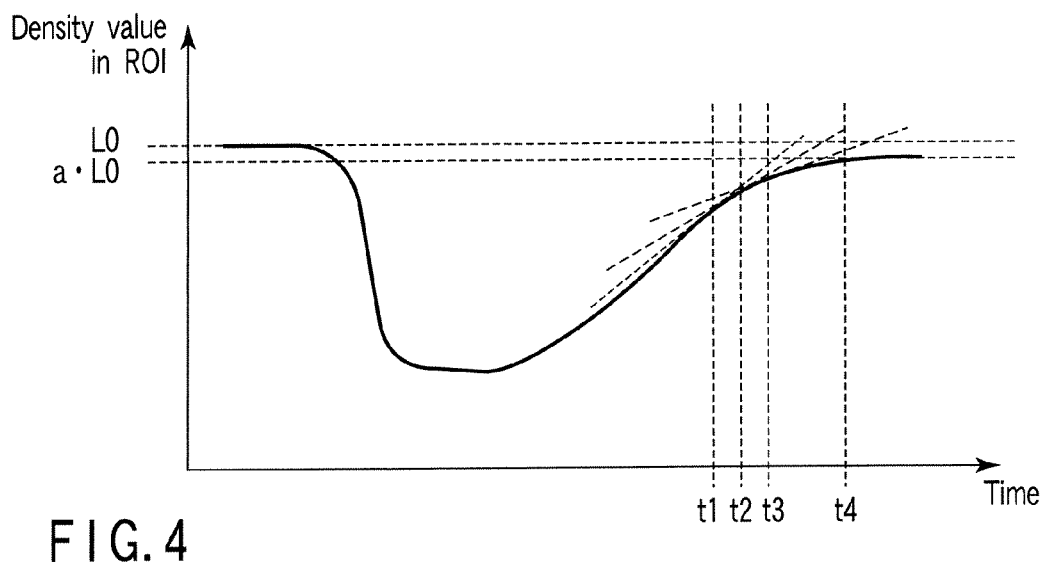
FIG. 4 is a graph showing a time density curve for complementing for radiography end determination processing by the system control unit in FIG. 1.

As exemplified by FIG. 4, the measured value of a differential image changes (decreases in FIG. 4) from an initial value L0 with time as a contrast medium flows into a radiography region or a region of interest, and returns to the initial value L0 as the contrast medium flows out. For this reason, a threshold approximate to the initial value L0 of density is set in advance to a·L0 where 0.9<a<1, and the system control unit 8 outputs an X-ray application stop signal to the high voltage control unit 20 at time t4 when a measured value has reached the threshold. The high voltage control unit 20 receives the X-ray application stop signal from the system control unit 8 and stops the application of a tube voltage from the high voltage generating unit 1 to the X-ray tube 21. When, for example, interval (C) has elapsed for, for example, 30 sec, the system control unit 8 outputs an X-ray application stop signal to forcibly finish the application of X-rays, even if a measured value is not equal to or less than the threshold.

It also suffices to determine the end of interval (C) on the basis of the slope of a density time curve indicated by the broken line in FIG. 4. That is, the system control unit 8 finishes interval (C) at time t3 when the slope of one of density time curves which the image computation/storage unit 10 has repeatedly calculated has reached a threshold approximated horizontally.

Note that the image computation/storage unit 10 has various image processing functions. For example, the image computation/storage unit 10 extracts an image necessary for myocardial perfusion from the images obtained in interval (B). For this purpose, the image computation/storage unit 10 specifies, for each heartbeat, an image, of the images acquired in interval (B), which is nearest to an end diastole. In interval (B), since images have been acquired at 30 fps, the maximum time shift error falls within 33 msec. This is a shift amount that poses no problem in myocardial perfusion measurement. The image computation/storage unit 10 generates a composite image by combining each of a plurality of images specified in interval (B) and an image selected from a plurality of images obtained in interval (C). The image computation/storage unit 10 generates a plurality of differential images by subtracting a control image in interval (A) from a plurality of composite images. Arraying and displaying the plurality of differential images in chronological order in interval (B) allow the operator to grasp the manner of how a contrast medium flows out.

According to the above description, intervals are automatically switched, i.e., the pulse rate (frame rate) is changed, depending on the start/end of the injection of a contrast medium. However, it suffices to manually switch pulse rates at an arbitrary time point in accordance with a pulse rate switching instruction issued by the operator using the operation unit 9.

According to the above description, the radiography period is divided into three intervals. However, it suffices to divide the period into two intervals by excluding first interval (A). In this case, an early frame in interval (B) is used as a control image.

In some case, after a differential image is obtained, quantitative evaluation is performed. In this case, a region of interest (ROI) is set on the image, and the corresponding value is read.

Note that if accuracy is required, it is preferable to consider the time difference between a blood vessel region of interest and a myocardial region of interest. That is, blood flows through a thick blood vessel first, and then reaches the cardiac muscle through a thin blood vessel. This produces a time difference. In practice, there is a time difference of about 300 msec to 1 sec. This time difference further increases in a patient having a morbid region. For this reason, when a blood vessel region of interest is set in a thick blood vessel, it is preferable to integrate the data of the region of interest from time 0 to (T−τ) and obtain data at time T with respect to the corresponding myocardial region of interest. When the operator wants to perform such strict operation, it is preferable to obtain two data per heartbeat in the above image acquiring operation. That is, X-ray pulses are applied twice per heartbeat.

Figure 5:
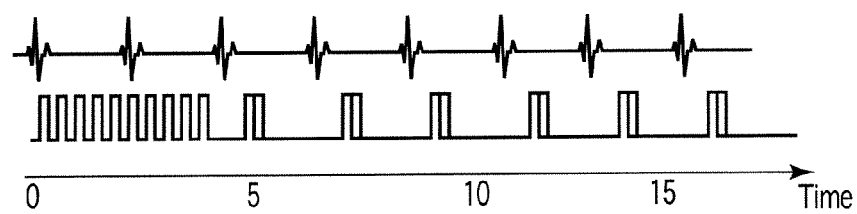
FIG. 5 is a view showing still another radiographing operation by the system control unit in FIG. 1.
Figure 6:
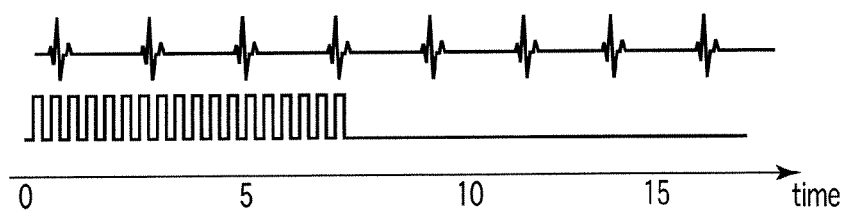
FIG. 6 is a view showing conventional radiographing operation.
Figure 7:
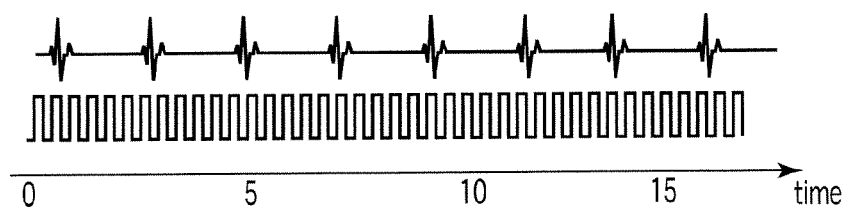
FIG. 7 is a view showing conventional radiographing operation.

If noise is to be further reduced in the above quantitative measurement, it suffices to perform averaging processing using adjacent frames. That is, as shown in FIG. 5, at the moment when the movement of the heart is small, a plurality of, for example, two pulse X-rays are integrally generated, and measurement is performed by using an image obtained by averaging two images acquired accompanying the operation. This reduces noise more than when using only one image. However, since a cardiac movement factor is added to the above measurement, it is necessary to output a plurality of pulses at the time when there is almost no cardiac movement. Alternatively, it suffices to use a motion correction unit.

It suffices to obtain an image of this myocardial perfusion and a quantitative numerical value even with a coarse spatial resolution. Therefore, for example, it suffices to use a myocardial perfusion image of a 256×256 matrix even with respect to a 1024×1024 matrix image as a raw image. For this reason, acquiring images by adding pixels in an ECG-gated acquisition interval allows a small amount of X-rays absorbed per pixel instead of a coarse image resolution. If, for example, four pixels are to be added, the X-ray dose is reduced to ¼.

In order to calculate myocardial perfusion, X-ray conditions must not change between frames. If the X-ray conditions change, the resultant image changes in density. This makes measurement meaningless. For this reason, the proposed acquisition method performs radiography so as to obtain at least one image per heartbeat upon setting the same kV value, mA value, and msec value.

Furthermore, another contrivance is to fix only the kV value while changing the mAs value. In this case, the mAs value is stored for each frame. When a myocardial perfusion image is to be generated, the image is corrected on the basis of the recorded mAs value. The reason why this operation holds is obvious from simple X-ray physical expressions, and variations in mAs are simply proportional to variations in density.

Various modifications can be made as follows.

Although an image density value is compared with a threshold to determine the end of final interval (C), it suffices to calculate a desired myocardial perfusion calculation value in real time and determine the end of the interval upon acquisition of data sufficient for calculation. Alternatively, it suffices to finish radiography when sufficient data are obtained in interval (C) or when data sufficient for the drawing of an approximate curve are obtained. In this case, it suffices to notify the operator of information indicating that he/she can finish radiography when sufficient data are obtained in interval (C), and to wait for an end instruction from the operator. This notification is performed by displaying a message or producing sounds like short beeps.

The image computation/storage unit 10 calculates a perfusion measurement value in real time during a radiography period and displays the value on a display unit 11.

The operator may manually switch between an interval in which pulse X-rays are generated at a constant cycle and an interval in which pulse X-rays are generated in the ECG-gated mode. For example, the radiography button provided on the operation unit 9 is a two-step button which switches the above intervals depending on how the operator presses it. The operation unit 9 has a sub-button. When the operator presses only the main button, pulse X-rays are generated at a constant cycle. When the operator simultaneously presses the main button and the sub-button, pulse X-rays are generated in synchronism with heartbeats. The sub-button may be located near the main button or far from the main button (a foot switch and a hand switch). When the operator releases the radiography button in the final interval, radiography is finished.

In the heartbeat synchronization mode, when one application (one pulse) is to be performed per heartbeat, the operator selects an end systole, end diastole, or middiastole for one application.

When two applications (two pulses) are performed per heartbeat, for example, the first application is performed a constant cycle of time after an R wave, and the second application is performed a different constant cycle of time after the R wave. It suffices to manage the constant cycle of time on the basis of an absolute time after an R wave or a relative time based on an R-R interval. Assume that the first application is performed in an end systole, end diastole, or middiastole, and the second application is performed at a timing preceding the first application by a predetermined time. Assume that the predetermined time is the time required for a contrast medium to flow from a measurement point A to a measurement point B.

Assume that three applications (three pulses) are performed per heartbeat. In this case, three pulses are adjacent to each other, and a plurality of obtained images are used for averaging. Assume that one application (one pulse) is performed per a plurality of heartbeats. When the heartbeat synchronization radiography time in interval (B) exceeds a predetermined time, the operation mode automatically shifts to the mode of performing one application (one pulse) per K heartbeats.

In the application of X-rays in the heartbeat synchronization mode, X-ray energy is made constant. Basically, the same kV and mAs values are used for all pulse X-rays. However, it suffices to set the same kV value and different mAs values. At this time, the mAs value is recorded, and is corrected in subsequent processing.

In the playback mode, the method of displaying the frame as seen easily is devised in playbacking. The playback rate is equal though the acquisition rate is different in interval A, B, and C. The images are acquired by the rate of one frame per a heart beat in interval A and C and the images are acquired by the rate of 30 fps in interval B. Images in interval B are playbacked by the rate of one flame per a heart beat. Therefore, the nearest cardiac phases are thinned out and displayed in interval B. As a result, the frame rate of interval A, B, and C becomes the same in the looking multiplication.

In the playback mode, the method of displaying the frame as seen easily is devised in playbacking. Because the acquisition rate is different in interval A, B, and C, two different moving images are playbacked. That is, the moving images of entire interval A, B, and C is playbacked by the rate of one flame per a heart beat, and moving images in interval B is playbacked by the rate of 30 fps. As a result, two moving images into which the frame rate doesn't change are displayed. Two moving images are separately stored. That is, the moving images of entire interval A, B, and C is stored by the rate of one flame per a heart beat, and the moving images of interval B is stored by the rate of 30 fps. As a result, the compound processing is not needed when the stored moving images are playbacked, and it is possible to be displayed as it is simply. The attribute information (frame rate etc.) is separately stored.

Second Embodiment

The second embodiment of the present invention will be described below with reference to the views of the accompanying drawing. First of all, the terms used in the following description will be defined as follows:

myocardial perfusion: including myocardial perfusion and myocardial blush, which are technically different from each other in a strict sense but are phenomena in which blood flows in/out to/from a capillary vessel to the cardiac muscle.

micro perfusion (micro circulation): a blood flow in a capillary vessel.

X-ray angiography apparatus: one of X-ray diagnostic apparatuses which is mainly used to perform angiography.

X-ray image: an image representing the intensity distribution of X-rays transmitted through a subject. This image is also called an X-ray image.

X-ray moving image: the data set of a series of X-ray images repeatedly radiographed by a two-dimensional detector over a time $t$.

coronary angiography: radiography of an X-ray image associated with a coronary artery lumen and enhanced by a contrast medium.

coronary artery: coronary pixel: a pixel in an acquired X-ray image.

fusion image: an image obtained by overlaying and combining X-ray images.

natural logarithm: Ln cardiac phase: a phase expressing the time of the current frame in % by marking R waves detected by an electrocardiographic signal and normalizing the time interval between an R wave and the next R wave by 100%. For example, a cardiac phase at an end systole is near 25%.

ROI: region of interest (Region Of Interest).

catheter room: almost synonymous with a catheter lab, catheter examination room, angiography examination room, and blood vessel intervention treatment room.

Figure 11:
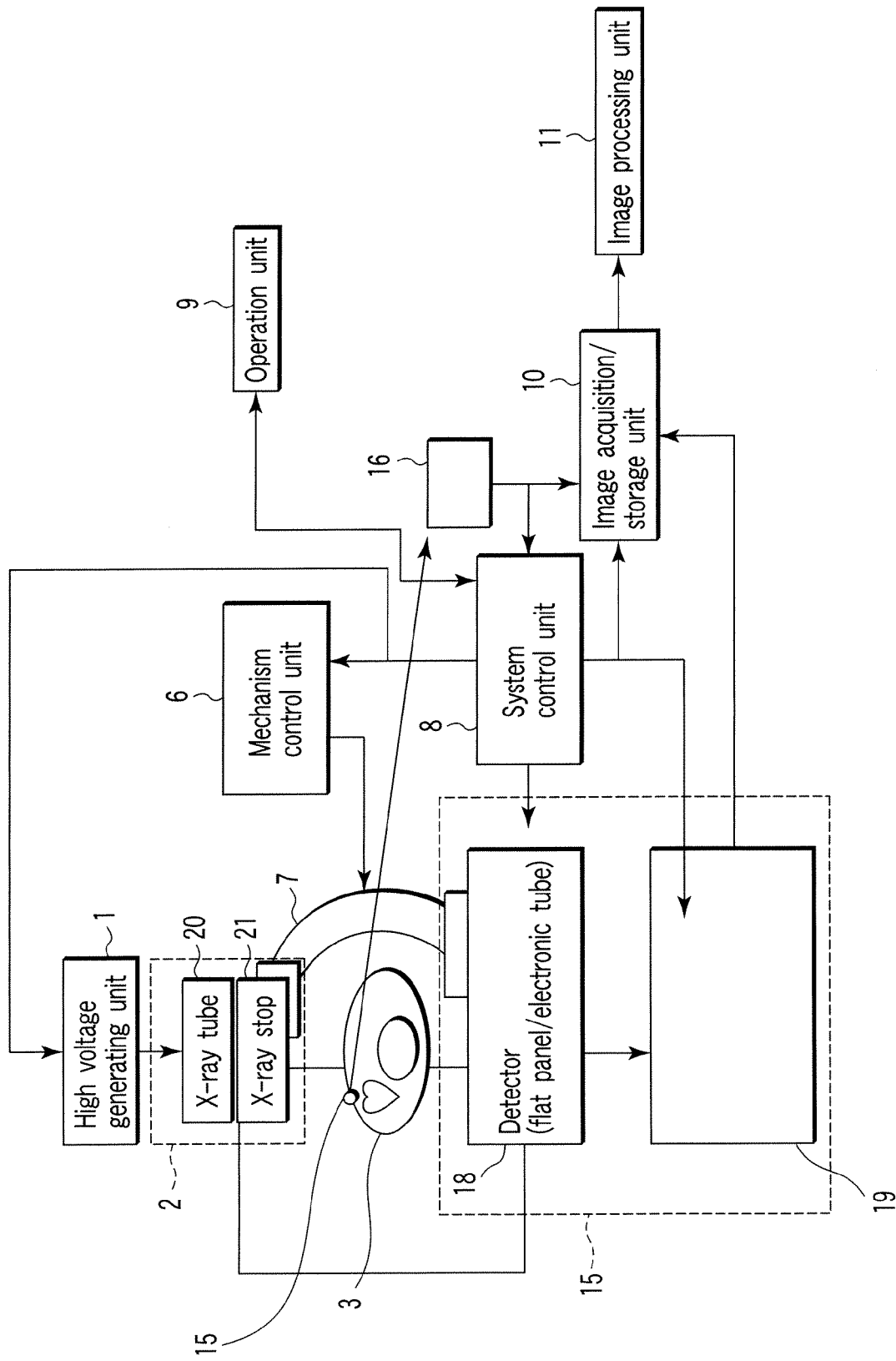
FIG. 11 is a view showing the details of a specific portion in FIG. 10.

FIG. 10 shows the outer appearance of an X-ray diagnostic apparatus according to this embodiment, more specifically an X-ray angiography apparatus in this case. FIG. 11 is a functional block diagram of this apparatus. The X-ray imaging apparatus includes a gantry 100. The gantry 100 includes a C-arm 7. The C-arm 7 is rotatably supported by a mechanism control unit 6. An X-ray generating unit 2 is mounted on one end of the C-arm 7. The X-ray generating unit 2 includes an X-ray tube 20 and an X-ray stop 21. A high voltage generating unit 1 generates a high voltage (tube voltage) applied between the electrodes of the X-ray tube 20, and generates a filament current supplied to the filament of the X-ray tube 20. A high voltage control unit 17 controls the tube voltage and/or the filament current generated by the high voltage generating unit 1 under the control of a system control unit 8.

An X-ray detection unit 5 is mounted on the other end of the C-arm 7. The X-ray detection unit 5 includes a detector 18 and an image data generating unit 19 which generates image data by processing an output from the detector 18. The detector 18 faces the X-ray tube 20 of the X-ray generating unit 2 through a subject 3 placed on a bed 4. The detector 18 is typically a solid flat panel detector comprising a two-dimensional array of a plurality of detection elements (pixels) which directly or indirectly convert incident X-rays into electric charges. The X-ray detection unit 5 repeats detecting operation of one cycle comprising accumulating electric charges, reading out electric charges, and resetting at a constant cycle under the control of the system control unit 8. An electrocardiogram monitor terminal 15 is attached to the subject 3. An electrocardiogram monitor reception unit 16 receives a signal from the electrocardiogram monitor terminal 15, and generates the data of an electrocardiogram of the subject 3. An operation unit 9 is connected to the system control unit 8. The operation unit 9 comprises a hand switch 12 and a user interface 14 including a display, a touch panel, and the like.

A computation processing unit 23 includes an image acquisition/storage unit 10 and an image processing unit 11. The image acquisition/storage unit 10 stores image data output from the X-ray detection unit 5 in association with cardiac phase data. The image processing unit 11 computes a plurality of indexes respectively representing the correlations of a plurality of time density curves concerning a plurality of local regions set in a myocardial region with respect to a time density curve (reference time density curve) concerning a reference region set on a coronary artery as a blood supply region for the cardiac muscle on the basis of the data of a plurality of images generated in a coronary angiography sequence, and generates an index map. The image processing unit 11 combines the map with a coronary artery image to generate a composite image. Note that a time density curve may be aimed at the density of an original image or the density (a value approximate to a contrast medium concentration) on the differential image between a mask image before the injection of the contrast medium and a contrast image after the injection of the contrast medium. The following description will exemplify the time density curve concerning the density on the differential image.

This embodiment provides three kinds of indexes.

A first index $K_1$ is calculated as "first index $K_1$ representing the inflow state of blood" concerning the local cardiac muscle with respect to the contrast medium inflow period from the start of the injection of the contrast medium to the end of the injection of the contrast medium when the reference time density curve of a coronary artery is set as an input function and the time density curve of the local myocardial region is set as an output function. A second index $K_2$ is calculated as "index $K_2$ representing the outflow state of blood" concerning the local cardiac muscle with respect to the contrast medium outflow period from the end of the injection of the contrast medium to the end of the radiography when the reference time density curve of a coronary artery is set as an input function and the time density curve of the local myocardial region is set as an output function. A third index $k_3$ is calculated from the indexes $K_1$ and $K_2$. Note that the time density curve at this time is defined as a signal component which is proportional to only the amount of contrast medium when the contrast medium injected into the human body is distributed to regions of interest (a coronary artery and the cardiac muscle in this embodiment) or passes through them.

Figure 12:
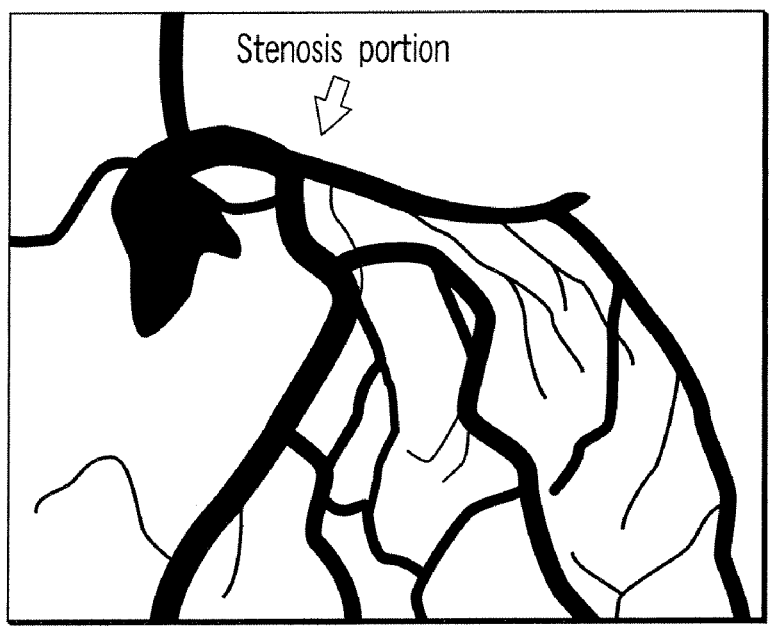
FIG. 12 is a view showing an example of a coronary angiographic image.
Figure 13:
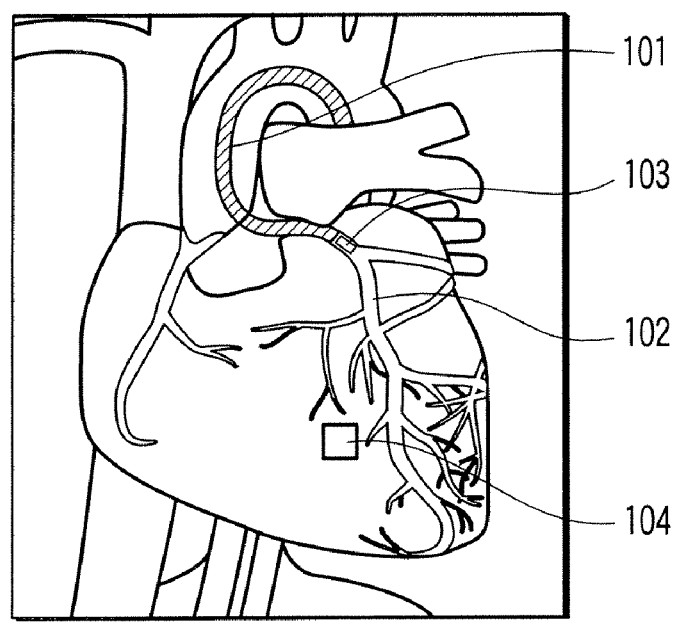
FIG. 13 is a view showing an ROI set on a coronary angiographic image in this embodiment.

FIGS. 12 and 13 exemplify coronary angiogram images (to be referred to as CAG images hereinafter) obtained by general X-ray angiography. Since a contrast medium exhibits a high absorbed X-ray dose, a CAG image allows to identify the shape of a coronary artery with the contrast being increased to discriminate it from other tissues (see FIG. 12). As shown in FIG. 13, the operator inserts a catheter 101 up to a coronary artery 102, and continuously injects a contrast medium for a predetermined time from the catheter 101 at this position. X-ray imaging is performed over the period from the start of the injection of a contrast medium to the lapse of a constant cycle of time after the end of the injection of the contrast medium.

When a contrast medium is injected into a coronary artery through the catheter 101, the X-ray diagnostic apparatus in FIG. 10 acquires X-ray images together with electrocardiograms. After the acquisition of images, the operator sets a reference region (myocardial blood supply region) 103 on a coronary artery and a plurality of local myocardial regions 104 on the cardiac muscle (blood supplied region) on a CAG image through the operation unit 9 (see FIGS. 32A and 33).

The plurality of local myocardial regions 104 are set on a myocardial region, and each typically have a plurality of pixels. A density corresponding to the amount of contrast medium in the local myocardial region 104 is typically calculated as a pixel average value. However, the local myocardial region 104 may have a single pixel. The myocardial blood supply region 103 typically has a rectangular shape having a width almost equal to or slightly smaller than that of a blood vessel, is set in an arbitrary direction along the blood vessel, and includes a plurality of pixels. A density corresponding to the amount of contrast medium in the myocardial blood supply region 103 is typically calculated as a pixel average value. The myocardial blood supply region 103 is set at an arbitrary portion on the channel between the injector and a myocardial region of interest, more specifically an arbitrary portion on the catheter or an arbitrary portion between the outlet of the catheter (corresponding to the entrance of a coronary artery) and the myocardial region of interest.

The image processing unit 11 generates a time density curve (TDC) concerning the myocardial blood supply region 103. Likewise, the image processing unit 11 generates a plurality of time density curves concerning a plurality of local myocardial regions 104. FIG. 34 shows the details of this generation process.

Figure 14:
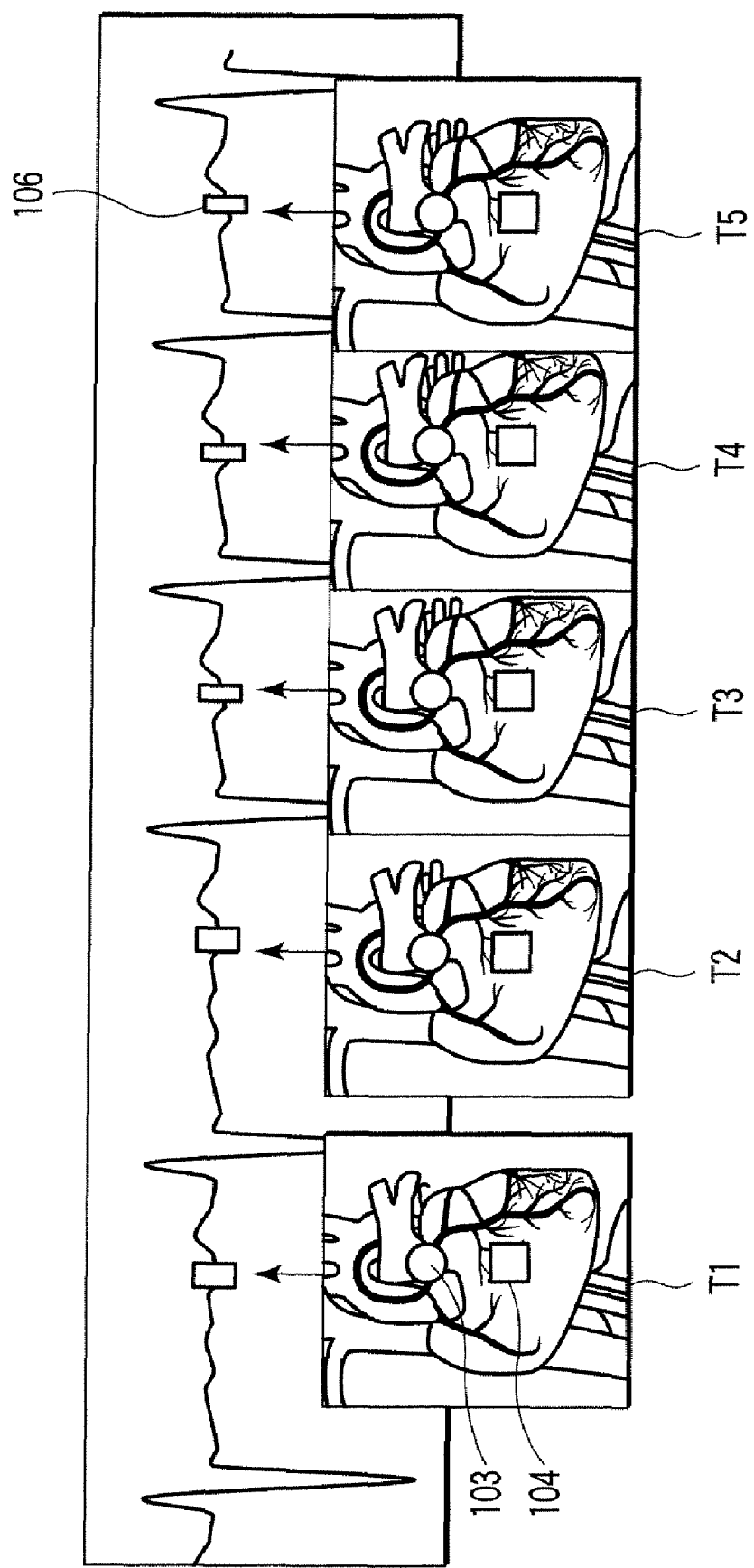
FIG. 14 is a view showing an image acquisition sequence in this embodiment.
Figure 21:
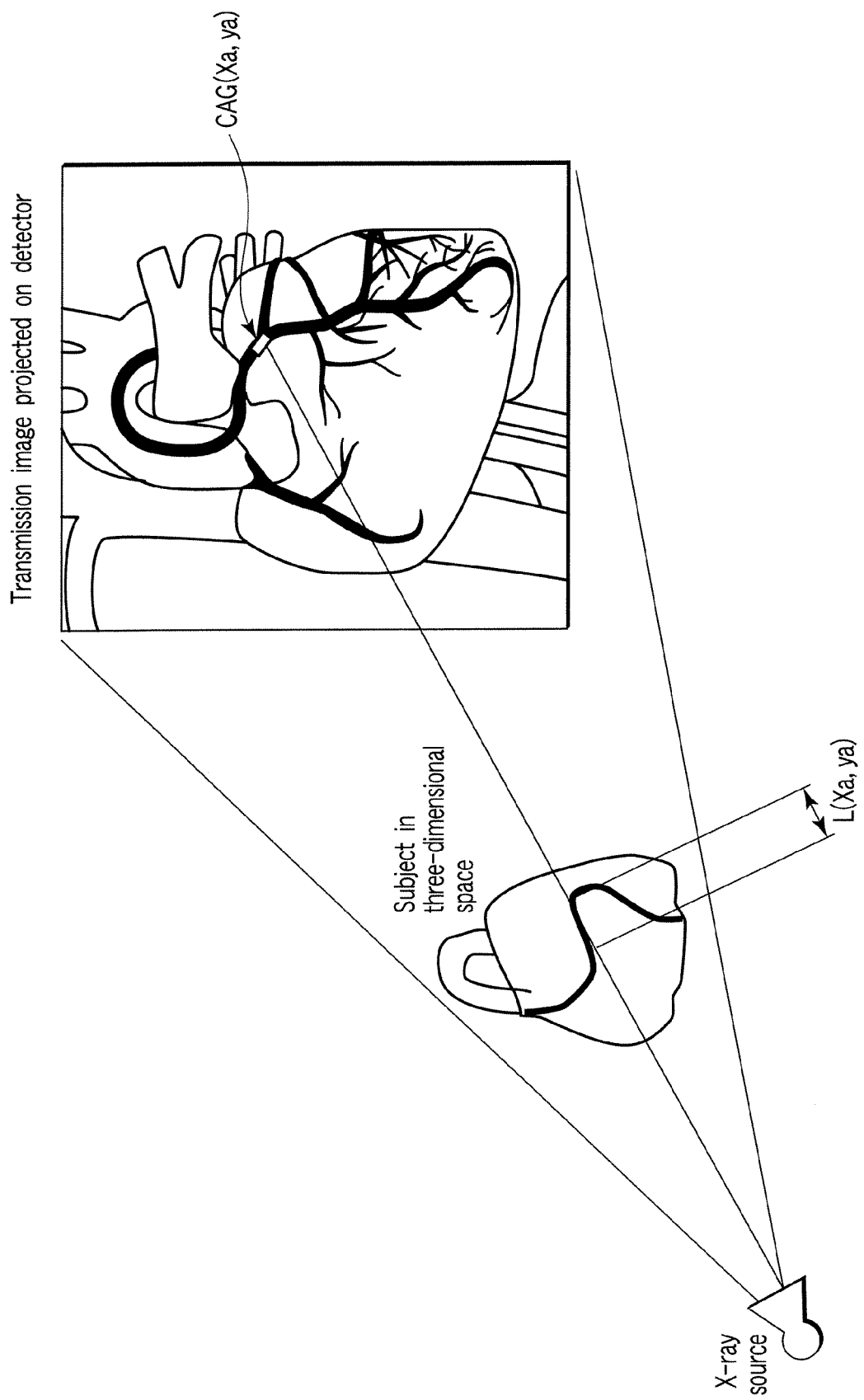
FIG. 21 is a supplementary view for the thickness effect of a transmission image in this embodiment.
Figure 32A:
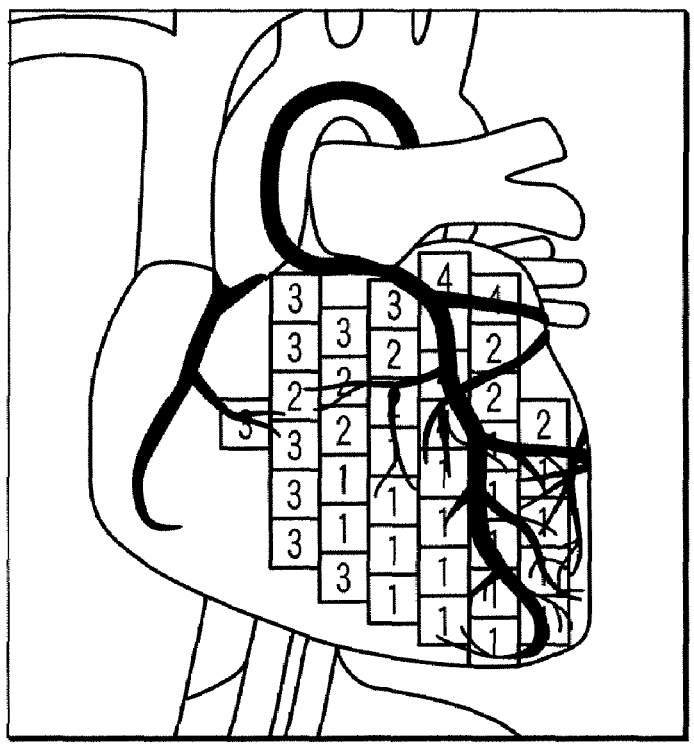
FIG. 32A is a view showing a myocardial function map generated from the two types of indexes $K_1$ and $K_2$ by the image processing unit in FIG. 11.
Figure 32B:
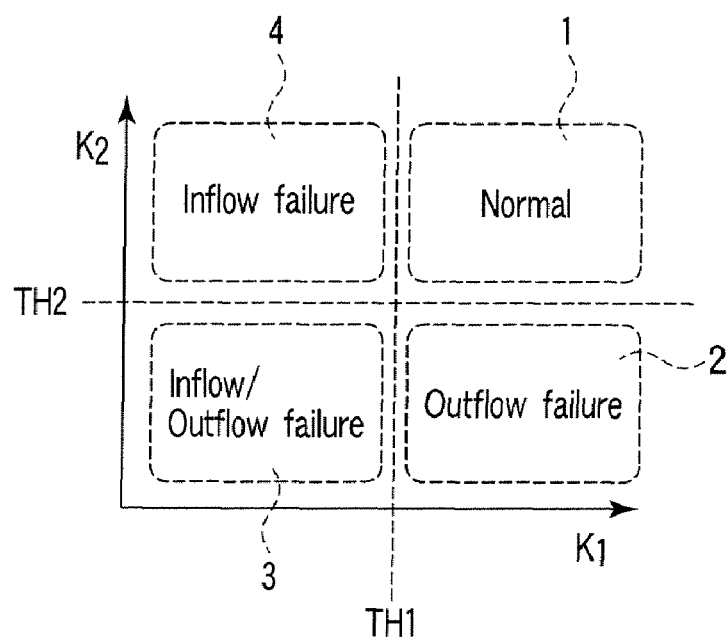
FIG. 32B is a view showing map codes in FIG. 32A.

Referring to FIGS. 32A and 32B, let CAG(x, y, t) be a pixel value at coordinates (x, y) of a CAG X-ray image at time t, and ln(CAG(x, y, t)) be the value obtained by calculating the natural logarithm of the pixel value in FIG. 34. Letting μ be an attenuation coefficient for a tissue or contrast medium per unit volume, and L be the distribution thickness of the tissue or contrast medium in the transmitting direction of X-rays in FIG. 21, the pixels in FIG. 14 satisfy the relation represented by ln(CAG(x, y, t))∝μL. The total amount of contrast medium distributed in a coronary artery or myocardial portion image recognized on the image in FIG. 13 which is a two-dimensional image is proportional to μL. That is, letting CAG(x, y, $t_0$) be the pixel value of an image T0 at time $t=t_0$ when there is no contrast medium, $$\ln(CAG(x,y,t))-\ln(CAG(x,y,t_0))$$

represents the total amount of contrast medium relatively distributed in the coronary artery or myocardial portion image in a series of images indicated by images T1 to T5 in FIG. 14 in proportion to the total amount of contrast medium distributed in the coronary artery or myocardial portion image recognized on the X-ray image in FIG. 13.

That is, since a CAG image is a transmission image from one direction, X-rays almost vertically strike the cardiac muscle near the center of the image, in general an examination target portion of the cardiac muscle which is located at the center of the image. This does not produce much thickness effect. In contrast, X-rays strike the cardiac muscle at a peripheral portion outside the center of the image in a direction near the tangent to the cardiac muscle, and hence a strong thickness effect appears. That is, the integral length of the contrast medium concentration at the peripheral portion becomes longer than that at the central portion. Consequently, the reliability of the contrast medium concentration measured at the peripheral portion of the heart is lower than that of the contrast medium concentration measured at the central portion. As described above, however, in general, the examination target portion of the cardiac muscle is positioned near the center of the image, and hence an index can be obtained with high reliability with respect to that portion. Note that it suffices to exclude, from display targets, any index concerning the peripheral portion of the heart which is not an examination target, separated from the center of the image by a predetermined distance, and exhibits poor reliability.

The myocardial blood supply region 103 in FIG. 14 is drawn in a circle for the sake of illustrative clarity. However, the shape of this region is set to a shape similar to a rectangle so as to enclose the coronary artery to measure the TDC when a contrast medium passes through the catheter 101, flows into the coronary artery, and mixes with arterial blood, as shown in FIG. 13. The local region 104 on the cardiac muscle is a dominant region of the coronary artery (a myocardial region which is activated by blood supplied through the coronary artery) in which a contrast medium is injected through the catheter 101. With regard to an entire myocardial portion in which the presence of a stenosis or microcirculation in a capillary vessel located ahead of the stenosis is suspected, pixels are sampled by using N×N pixels (N=odd numbers: 1, 3, 5, . . . ) with, for example, N=5, represented by the region of interest 104, and the computation result (to be described later) obtained by smoothing processing with a size of 5×5, i.e., the central position of the resultant pixel, is recorded as a representative position.

[Observation]

As described above, the value to be observed is ln(CAG(x, y, t))−ln(CAG(x, y, $t_0$)).

In this case, let Ca(t) be the reference TDC of a relative contrast medium concentration per unit blood vessel volume concerning the myocardial blood supply region 103, and Cmyo(t) be a relative contrast medium concentration per unit myocardial volume. The relationship between the observed value, Ca, and Cmyo is represented by the following mathematical expression. Note that since Ca represents a differential value between values before and after the injection of the contrast medium, an initial value Ca(0) is 0 value.

$$Ca(t) \times L(x_a, y_a) = \ln(CAG(x_a, y_a, t)) - \ln(CAG_0(x_a, y_a, t_0)) \quad (1)$$

In this case, $(x_a, y_a)$ is a pixel in the local region of interest 103 set on the upstream side of the coronary artery in FIG. 13, and represents an average value or a total amount in the region of interest. Although it suffices to use either of these values, a selected one of them is used in the following operation. That is, they are not in a mixed manner. Let t be the time in sec, and a means an artery.

$$Cmyo(t) \times L(x_{myo}, y_{myo}) = \ln(CAG(x_{myo}, y_{myo}, t)) - \ln(CAG_0(x_{myo}, y_{myo}, t_0)) \quad (2)$$

In this case, $(x_{myo}, y_{myo})$ is a pixel in the region of interest 104 set in the cardiac muscle shown in FIG. 13, and represents an average value or a total amount in the region of interest 104. A plurality of regions of interest 104 are a plurality of local regions having the same shape and size, which are obtained by dividing a perfusion computation range 105 set on a CAG image through the operation unit 9 shown in FIGS. 15A and 15B into the regions shown in FIGS. 32A and 33. Note that the subscript "myo" means myocardium.

[Model]

As an inflow/outflow model of a contrast medium in/from the cardiac muscle, (theory 1) to be described later is introduced. This makes it possible to obtain the following relation:

$$C_{myo}(t) = K_1 \times \int_0^T C_a(t)dt + p \quad (3)$$

[Adaptation of Observed Value to Model]

Images T1 to T5 are CAG images, of the CAG images radiographed by a series of operations in the ECG-gated mode, which correspond to a specific cardiac phase 106. Assume that the corresponding acquisition times are t1, t2, . . . , t5. With regard to the set of ECG-gated images T1 to T5, the image processing unit 11 performs processing described by mathematical expressions (1), (2), and (3) induced in [Observation] and [Model].

$$[\ln(CAG(x_{myo}, y_{myo}, t)) - \ln(CAG(x_{myo}, y_{myo}, t_0))] = \frac{L_{myo}(x_{myo}, y_{myo})}{L_a(x_{myo}, y_{myo})} \quad (4)$$

$$K_1 \times \int_0^T [\ln(CAG(x_a, y_a, t)) - \ln(CAG_0(x_a, y_a, t_0))]dt + p$$

Wherein $$X(t) = \int_0^T [\ln(CAG(x_a, y_a, t)) - \ln(CAG(x_a, y_a, t_0))]dt$$

when $$Y(t) = \ln(CAG(x_{myo}, y_{myo}, t)) - \ln(CAG(x_{myo}, y_{myo}, t_0)),$$

$$K_1' = \frac{L_{myo}(x_{myo}, y_{myo})}{L_a(x_{myo}, y_{myo})} K_1,$$

$$Y(t) = K_1' \times X(t) + p \quad (5)$$

Figure 16:
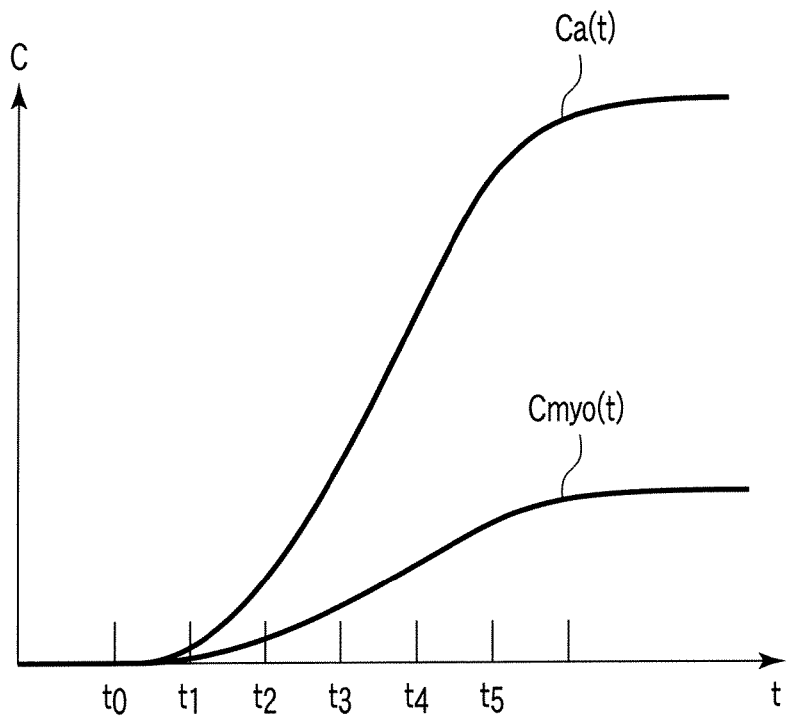
FIG. 16 is a graph showing a time density curve in a contrast medium inflow period, which is generated by an image processing unit in FIG. 11.

The image processing unit 11 calculates an index $K_1'$ reflecting the manner of actual inflow of blood into a local myocardial region, which is proportional to a myocardial blood flow. First of all, the image processing unit 11 sets a contrast medium inflow period from the time point when injection of a contrast medium through the catheter starts to the time point when the injection of the contrast medium is complete as a calculation target period for the index $K_1'$. As shown in FIG. 16, the image processing unit 11 generates a time density curve Ca(t) concerning the myocardial blood supply region 103 and a plurality of time density curves Cmyo(t) concerning a plurality of local myocardial regions 103 from a plurality of X-ray images acquired in this contrast medium inflow period.

Figure 17:
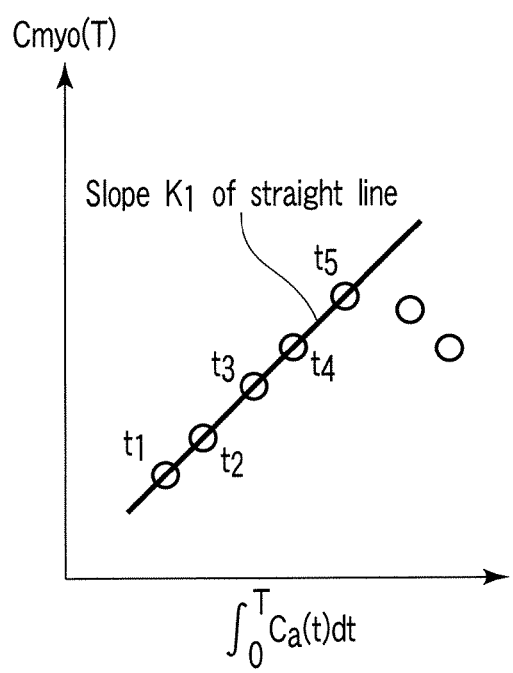
FIG. 17 is a graph showing an index $K_1$ calculated by the image processing unit in FIG. 11.

As shown in FIG. 17, the image processing unit 11 then plots the value of a contrast medium abundance Cmyo(t) in the local myocardial region 104 at each time on the ordinate with the abscissa representing a time integral value (the inflow amount of contrast medium) ∫Ca(t) of the contrast medium passing through the myocardial blood supply region 103. That is, the image processing unit 11 generates the discrete distribution of temporal changes in the intake amount of blood in a local myocardial region with respect to the amount of blood supplied to the entire cardiac muscle. The image processing unit 11 calculates the index (first index) $K_1'$ as the slope of a straight line by performing straight-line fitting for this discrete distribution. The index $K_1'$ is a quantified value representing how much the local myocardial region receives blood following up the supply of blood to the entire cardiac muscle. When the index $K_1'$ deviates from a normal range to the lower value side, it indicates that the inflow of blood into the local myocardial region may not follow up the inflow of blood into the coronary artery, i.e., the local myocardial region may suffer inflow failure. When the index $K_1'$ deviates from a normal range to the higher value side, it indicates that the local myocardial region may suffer outflow failure. The image processing unit 11 calculates indexes $K_1'$ for all the local regions 104 by similar processing, and generates an index $K_1'$ map. The image processing unit 11 can generate a composite image by superimposing (fusing) the obtained map or a CAG image and display the composite image on a display unit 24. This allows the operator to determine the myocardial function together with a positional relationship with myocardial tissue.

Modification A)

According to the above description, the series of the ECG-gated CAG images T1 to T5 are extracted from consecutive images. However, in order to reduce radiation exposure for a patient, it suffices to control the apparatus in FIG. 10 so as to generate X-rays only in specific electrocardiographic phases at the time of radiography, hereby acquiring only a set of images necessary for (theory 1) to be described later.

Modification B)

Figure 18:
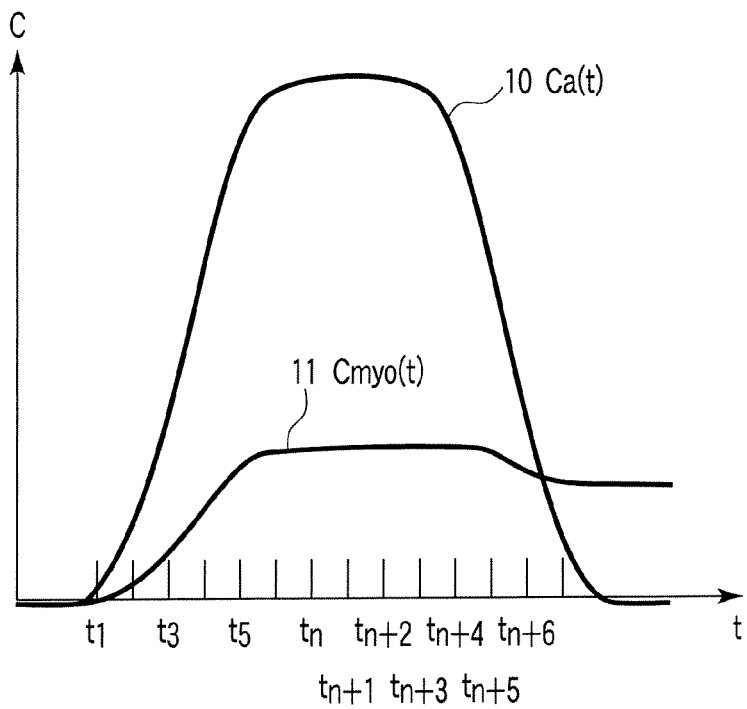
FIG. 18 is a graph showing a time density curve in a radiography period, which is generated by the image processing unit in FIG. 11.
Figure 19:
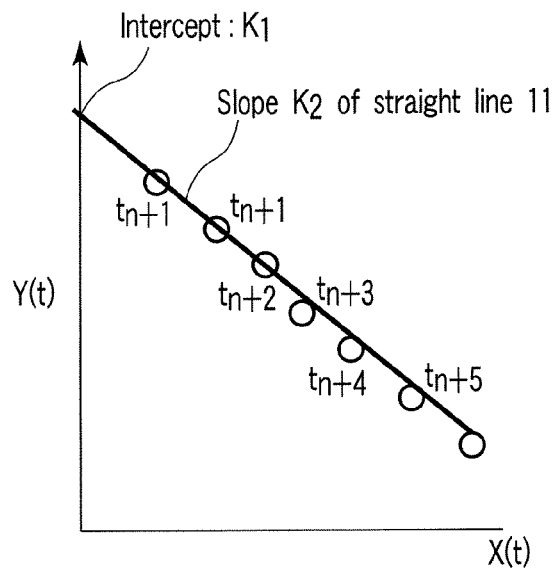
FIG. 19 is a graph showing an index $K_2$ calculated by the image processing unit in FIG. 11.

According to (theory 2) to be described later, it is possible to measure a blood flow and a backdiffusion of a contrast medium from the cardiac muscle (the amount of contrast medium flowing back from the cardiac muscle to a blood vessel) on the basis of $K_1$ and $K_2$ obtained from a series of TDC curves (FIG. 18) in the outflow period between the instant at which the contrast medium reaches the cardiac muscle and the instant at which the contrast medium is discharged by the graphic plot method shown in FIG. 19, and to display the measurement result in the same manner as described above by using the technique shown in FIGS. 15A and 15B. Likewise, in order to reduce radiation exposure for the patient at time $t_n$, it is possible to control the apparatus in FIG. 10 so as to generate X-rays only in specific electrocardiographic phases at the time of radiography, thereby acquiring only a set of images necessary for theory 1.

Modification C)

Figure 29A:
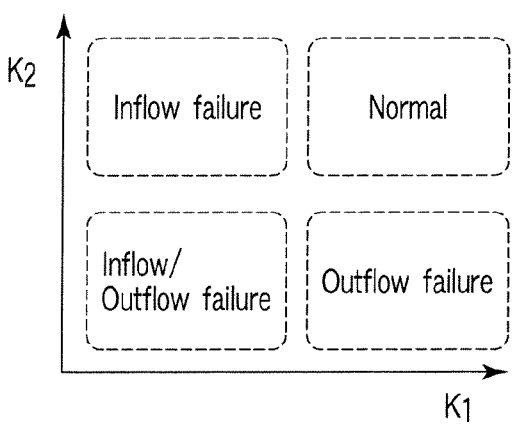
FIG. 29A is a view showing the distribution of two types of indexes generated by the image processing unit in FIG. 11.

In addition, calculating and displaying the ratio ($K_1/K_2$) between $K_1$ and $K_2$ allow quantification (automation) of the classification method disclosed in C. Michael Gibson, MS, MD; Christopher P. Cannon, MD; Sabina A. Murphy, MPH; Kathryn A. Ryan, BS; Rebecca Mesley, BS; Susan, J. Marble, RN, MS; Carolyn H. McCabe, BS; Frans Van de Werf, MD, PhD; Eugene Braunwald, MD; for the TIMI (Thrombolysis In Myocardial Infarction) Study Group, Relationship of TIMI Myocardial Perfusion Grade to Mortality After Administration of Thrombolytic Drugs, Circulation. 2000: 101: 125-130. That is, it is possible to perform automatic classification according to the classification table in FIG. 28 or plot the relationship between the indexes $K_1$ and $K_2$ as indicated by the graphs shown in FIGS. 29A and 29B.

Modification D)

By using this embodiment, two types of series of ECG-gated CAG images are acquired from the same patient in the same direction. That is, as shown in FIGS. 20A and 20B, myocardial blood flow images 205 at rest (=Prest(x, y)) and myocardial blood flow images 206 under drug stress (=Pstress(x, y)) after the administration of a drug having the effect of increasing a myocardial blood flow, e.g., adenosine, are acquired. If (myocardial blood flow images 206)/(myocardial blood flow images 205)=Pstress(x, y)/Prest(x, y) is defined as a comparison image between images at rest and under stress, since the myocardial blood flow images 205 and 206 exhibit the same myocardial thickness at the same position (x, y) at which images are acquired in the same direction, division of the images will approximately cancel them. This makes it possible to obtain a blood flow increase ratio (myocardial Flow reserve) per unit myocardial volume.

$$\text{blood flow increase ratio} = \frac{K'_{1\,stress}}{K'_{1\,rest}} = \frac{\frac{L_{myo}}{L_a}K_{1stress}}{\frac{L_{myo}}{L_a}K_{1rest}} = \frac{K_{1stress}}{K_{1rest}}$$

Likewise, measuring an index $K'_{before}$ before a treatment for stenosis or the like and an index $K'_{after}$ after the treatment and dividing them can obtain a blood flow increase ratio (a recovery ratio by the treatment) per unit myocardial volume.

Modification E)

Figure 27:
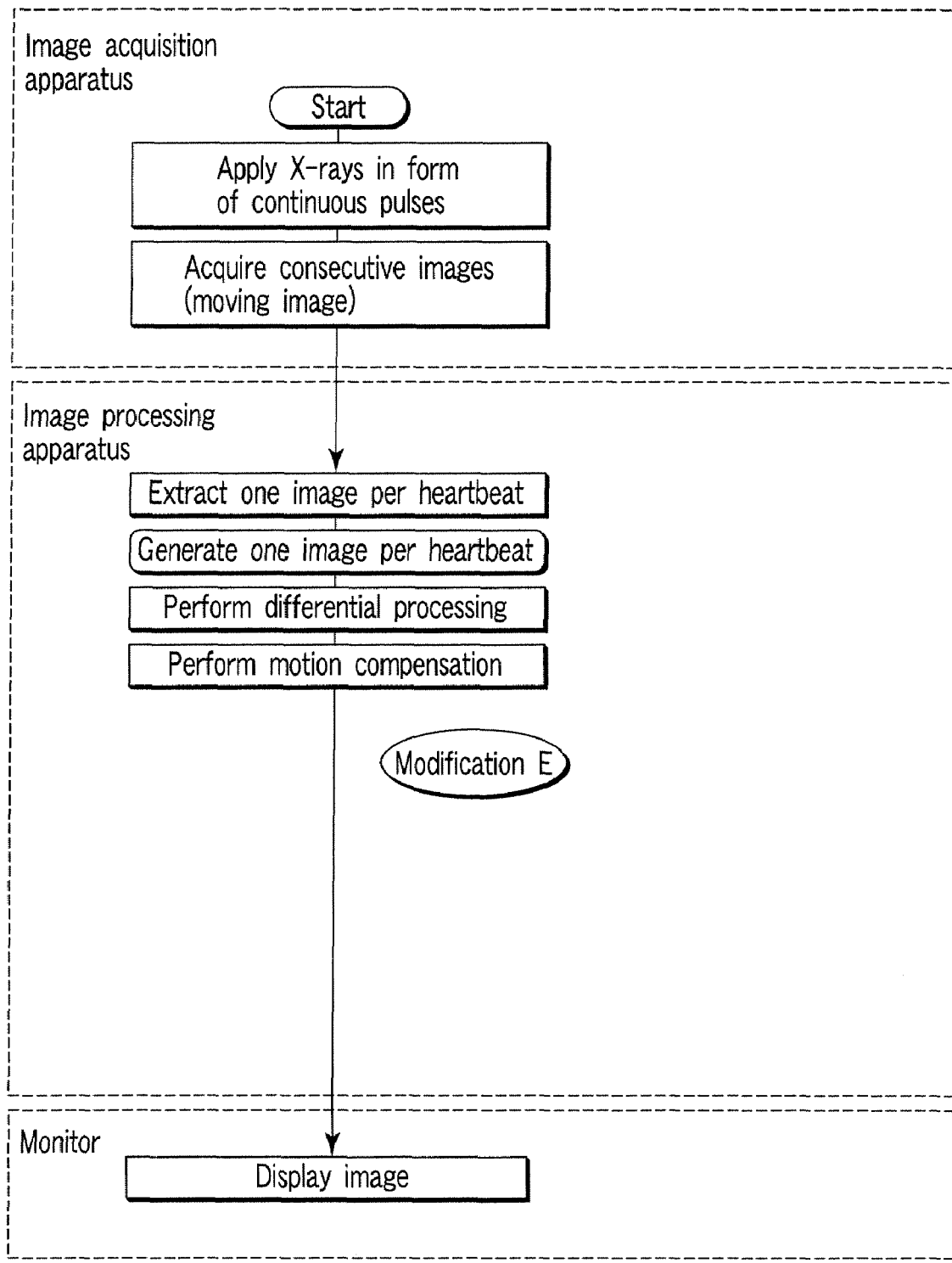
FIG. 27 is a flowchart showing still another processing procedure in this embodiment.

According to this embodiment, as exemplified by FIG. 27, even if [theories 1 and 2] to be described later are not completely computed, since an image given by Cmyo(t)−Cmyo($t_0$) represents a blood flow to the cardiac muscle when Cmyo(t)=ln(CAG(x, y, t))−ln(CAG(x, y, $t_0$)), this differential moving image can be displayed only at the same examination time. In this case, $t_0$=time immediately before injection of contrast medium.

(Theory 1)

Figure 31:
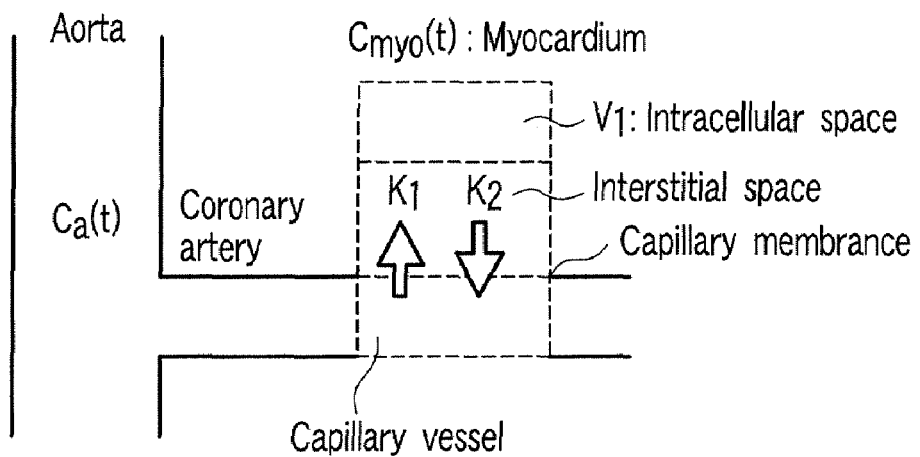
FIG. 31 is a view for explaining indexes $K_1$ and $K_2$ in this embodiment.

Let Cymo(t) be a relative contrast medium concentration in a cardiac muscle portion at time $t$, Ca(t) be a relative contrast medium concentration time curve in a coronary artery blood, KK1 be a myocardial blood inflow, and KK2 be a myocardial blood outflow. Referring to FIG. 31, the mass balance between the contrast medium in the cardiac muscle portion and that in coronary artery blood can be expressed by mathematical expression (6).

$$\frac{dC_{myo}(t)}{dt} = K_1 C_a(t) - k_2 C_{myo}(t) \quad (6)$$

A blood flow in a cardiac muscle portion or a parameter correlating with a blood flow can be calculated by the Patlak plot method using a phenomenon in which a contrast medium flows into the cardiac muscle portion, which will be described below. Under a condition ($0 \leq t \leq MTT$) (MTT=mean transit time=a mean transit time taken for a contrast medium to flow from an artery into the cardiac muscle and flow out to a vein, which is generally about 5 to 10 sec in the cardiac muscle) in which a contrast medium begins to flow into a cardiac muscle portion, an outflow amount $k_2 C_{myo}(t)$ is very small, and the conditions represented by $C_{myo}(t) \approx 0$ and $K_1 Ca(t) >> K_2 C_{myo}(t)$ hold. At this time, Eq. (6) can be simplified as follows:

$$\frac{dC_{myo}(t)}{dt} \cong K_1 C_a(t) \quad (7)$$

When the mathematical expression (7) is integrated, the following mathematical expressions is obtained.

$$C_{myo}(t) = K_1 \times \int_0^T C_a(t)dt + p \quad (8)$$

When $C_{myo}(\ )$ is plotted on Y-axis and $$\int_0^T C_a(t)dt$$

is plotted on X-axis, a line gradient represents $K_1$.

$K_1$ represents a transition constant (sec$^{-1}$) or (ml/min/g) concerning the transition of a contrast medium from blood to a myocardial interstitial portion and is proportional to a blood flow.

Rutland MD. A single injection technique for subtraction of blood background in 131I-hippuran renograms. Br J Radiol 1979; 52: 134-137.

Patlak C S, Blasberg R G, Fenstermacher J D. Graphical evaluation of blood-to-brain transfer constants from multiple-time uptake data. J Cereb Blood Flow Metab 1983; 3:1-7.

(Theory 2)

Let Cymo(t) be a relative contrast medium concentration in a cardiac muscle portion at time $\underline{t}$, and Ca(t) be a relative contrast medium concentration in a coronary artery blood. Referring to FIG. 31, the mass balance between the contrast medium in the cardiac muscle portion and that in coronary artery blood can be expressed by mathematical expression (9).

$$\frac{dC_{myo}(t)}{dt} = K_1 C_a(t) - k_2 C_{myo}(t) \quad (9)$$

A blood flow in a cardiac muscle portion or a parameter correlating with a blood flow can be calculated by a method using a clearance during which the contrast medium flows out from the cardiac muscle. Integrating Eq. (9) yields (10).

$$C_{myo}(t) = K_1 \int_0^t C_a(\tau)d\tau - k_2 \int_0^t C_{myo}(\tau)d\tau \quad (10)$$

When mathematical expression (10) is divided by $$\int_0^t C_a(\tau)d\tau,$$

the following mathematical expressions is obtained.

$$Y(t)=K_1-k_2X(t) \quad (11)$$

Wherein $$Y(t) = C_{myo}(t) \Big/ \int_0^t C_a(\tau)d\tau,$$

-continued and $$X(t) = \int_0^t C_{myo}(\tau)d\tau \Big/ \int_0^t C_a(\tau)d\tau$$

When Y(t) and X(t) are respectively plotted on the Y- and X-axes, the slope of a straight line represents $K_2$, and an intercept on the Y-axis represents $K_1$. $K_1$ represents a transition constant (sec$^{-1}$) or (ml/min/g) concerning the transition of a contrast medium from blood to a myocardial interstitial portion and is proportional to a blood flow. $K_2$ represents a transition constant (sec$^{-1}$) concerning the transition of a contrast medium from a myocardial interstitial portion to blood (see the following reference together with FIG. 31).

Yokoi T, Iida H, Itoh H, Kanno I. A new graphic plot analysis for cerebral blood flow and partition coefficient with iodine-123-iodoamphetamine and dynamic SPECT validation studies using oxygen-15-water and PET. J Nucl Med 1993; 34:498-505.

(Flowchart of Actual Processing)

An example of a flowchart of actual image processing will be described below. The following method is an example. It suffices to use another processing method based on the above theories.

Figure 22:
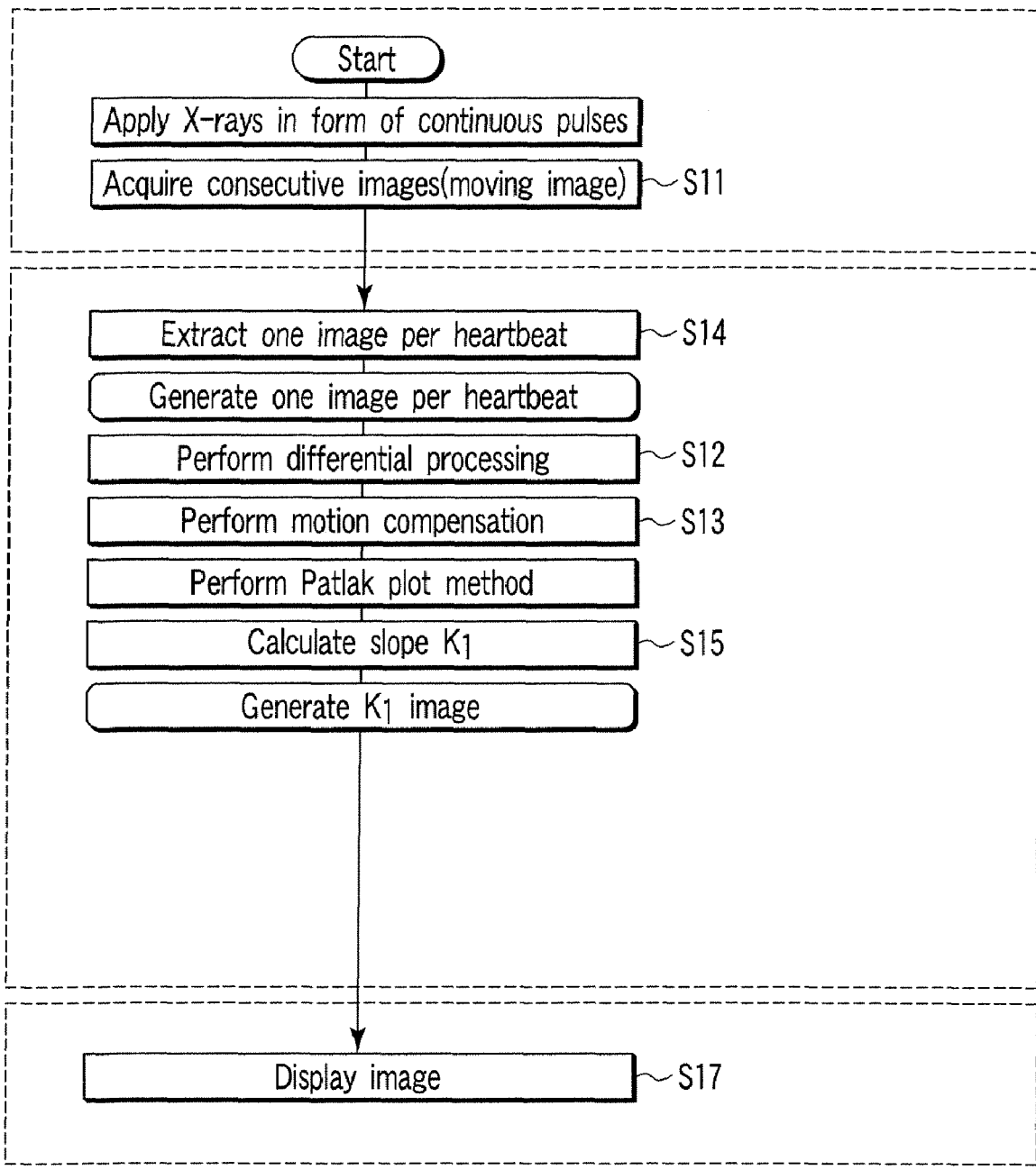
FIG. 22 is a flowchart showing a processing procedure in this embodiment.

A specific overall processing flowchart of this embodiment will be described with reference to FIG. 22. An X-ray image is characterized by being a moving image of an angiographed subject (S11). For example, a moving image has a duration of 3 to 60 sec and includes 10 to 30 images per sec. Images are radiographed in the same direction under the same X-ray conditions. Assume that there is no movement of the patient and bed during radiography.

The image processing unit 11 extracts one image corresponding to a specific cardiac phase per heartbeat (S14), and performs differential processing of the image from an image corresponding to the same cardiac phase before the injection of the contrast medium (S12). More specifically, if there are a plurality of images corresponding to the same cardiac phase before the injection of the contrast medium, the image processing unit 11 performs differential processing for an image obtained by averaging the images.

The image processing unit 11 performs motion compensation processing (S13). The image processing unit 11 detects a motion compensation amount by pattern matching processing with reference to image patterns (blood vessel, cardiac wall, and catheter patterns). With regard to a frame having no feature pattern, a movement amount obtained in the same phase at different times is used as a substitute. For motion compensation, this embodiment has a table which is used to move an entire image or allows to know where an ROI is moved. Motion compensation also compensates for the slight body movement of the patient and respiratory movement.

The operator designates a specific cardiac phase in advance through the operation unit 9. For example, the operator designates a specific cardiac phase at an end diastole. Of many frames obtained by pulse radiography, a frame closest to the corresponding time is extracted. Note that it suffices to use different cardiac phases for the density time curve Ca in the blood supply region 103 and the density time curve Cmyo in the local myocardial region 104. Cmyo(t+T) is used for Ca(t). In this case, T represents a delay value necessary for a contrast medium to flow from the blood supply region 103 to the local myocardial region 104. More specifically, the delay value T is often set to about 1 to 30 frames (1/30 to 1 sec). This delay time is generally called a TIMI frame count (TFC) or corrected TIMI frame count (CTFC).

The image processing unit 11 calculates an index $K_1$ as a slope representing the correlation of Cmyo(t) with respect to a density time integral $\Sigma ca(t)$ (S15). As exemplified by FIG. 17, the image processing unit 11 performs fitting to calculate a regression line. The image processing unit 11 calculates this regression line only in a predetermined time interval. This predetermined interval is determined in synchronism with the contrast medium injector. Letting J1 be the start time of the injection of a contrast medium from the injector and J2 be the end time of the injection, a start time t1 of a predetermined interval is set to, for example, t1=J1+1 sec, and the end time of the predetermined interval is set to J2+2 sec. Alternatively, the predetermined interval may be determined from the value of an image. That is, the time when the TDC rises is set to t1, and the time when the TDC becomes flat is determined as the end of the predetermined interval. The image processing unit 11 calculates a correlation value with the regression line. It is preferable to exclude a heartbeat including an irregular pulse from calculation. The image processing unit 11 calculates one $K_1$ for each moving image. However, in order to speed up the processing, it suffices to use a technique of calculating $K_1$ as needed for each frame. As described above, as a given pixel value, the average value (or median) of neighboring N×M pixels is set instead of the value of the pixel of interest itself. The display unit 24 displays a blood flow image (S17). The display unit 24 displays an index $K_1$ map. The display unit 24 may display the $K_1$ map upon converting density values into color values. It suffices to display an acquired original moving image first and then superimpose and display the $K_1$ map immediately after that. Alternatively, it suffices to display the original image and the $K_1$ map side by side.

Figure 23A:
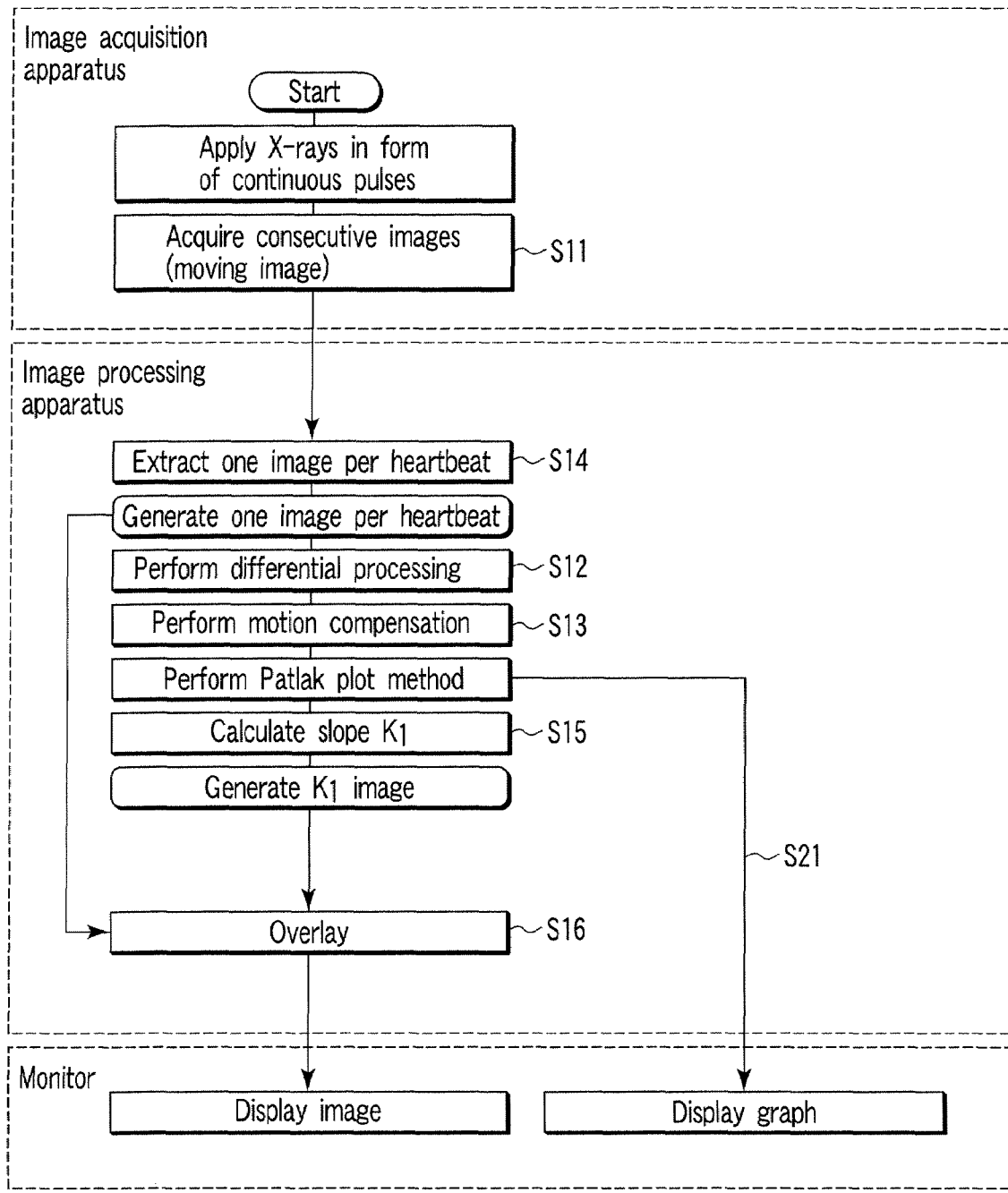
FIG. 23A is a flowchart showing another processing procedure in this embodiment.
Figure 23B:
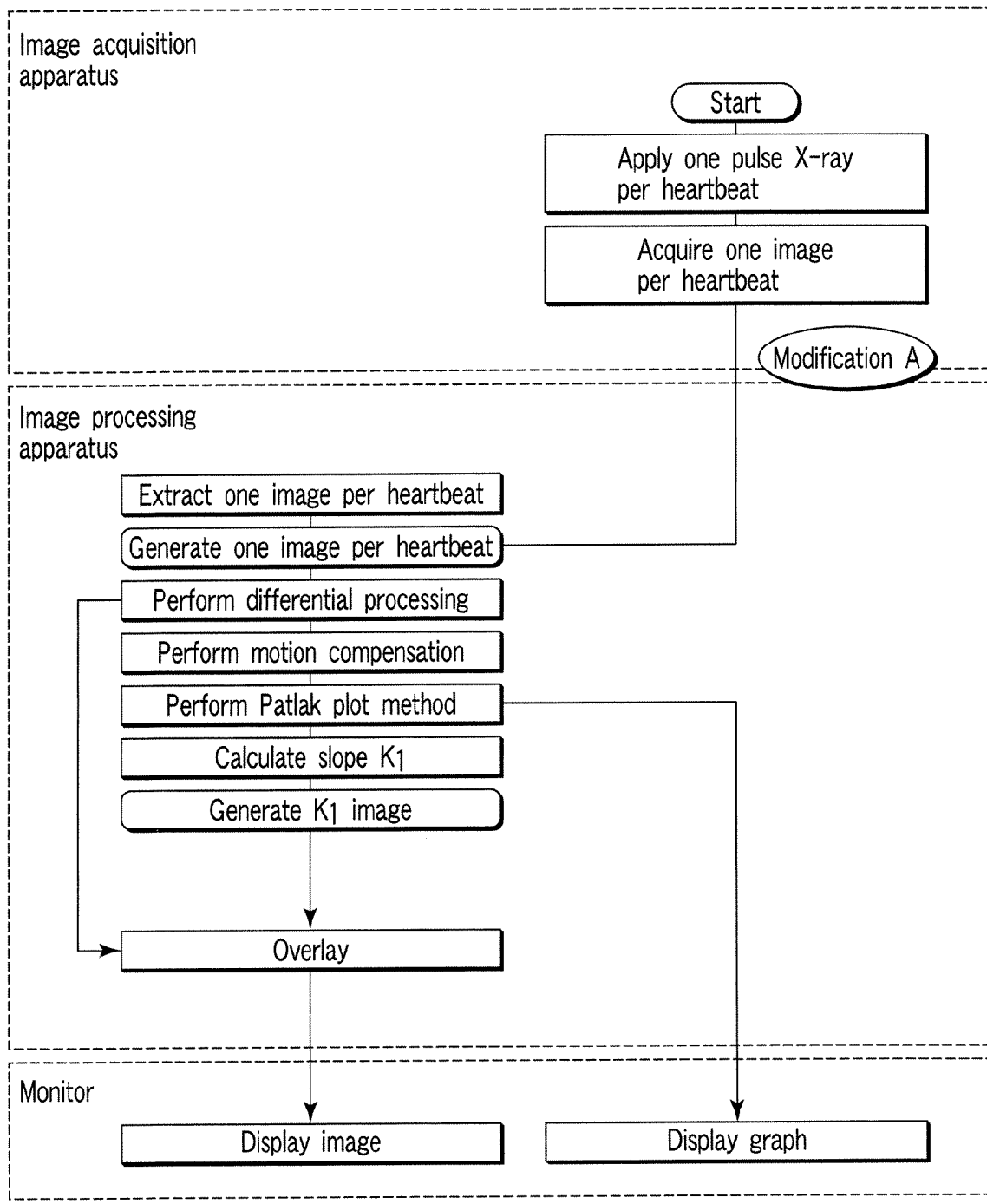
FIG. 23B is a flowchart showing still another processing procedure in this embodiment.

In correspondence with modification A), this embodiment may integrate image processing in the X-ray diagnostic apparatus (FIGS. 10 and 22) or provide it as an image processing apparatus (FIGS. 30 and 23) independent of the X-ray diagnostic apparatus. The display unit superimposes and displays an original image (a blood vessel image or radiographed image) on a blood vessel image (an index image or map image) (S16). The display unit superimposes and displays a monochrome original image (blood vessel image) on a color blood vessel image obtained by directly assigning indexes to a color table. Note that the original image is a moving image, and a color blood flow still image may be superimposed on a blood vessel moving image. In practice, a color blood flow still image is superimposed on a blood vessel still image. In order to generate a still image from a moving image, the densest one of the frames of the moving image is selected or an image is generated by detecting the smallest one of the pixel values of the moving image for each pixel. Assume that the original image is an image before or after differential processing. This embodiment is characterized by displaying a graph (S21). With regard to a specific ROI (x, y), the graphs in FIGS. 16 to 19 are displayed. The graphs in FIGS. 17 and 18 display the slope, intercept, and correlation value of a fitting function (regression line). The operator designates the blood supply region 103. This embodiment comprises the graphical user interface 14 for designating the blood supply region 103 on an image. One pulse X-ray is applied in a specific cardiac phase of one heartbeat (FIG. 23).

Figure 24:
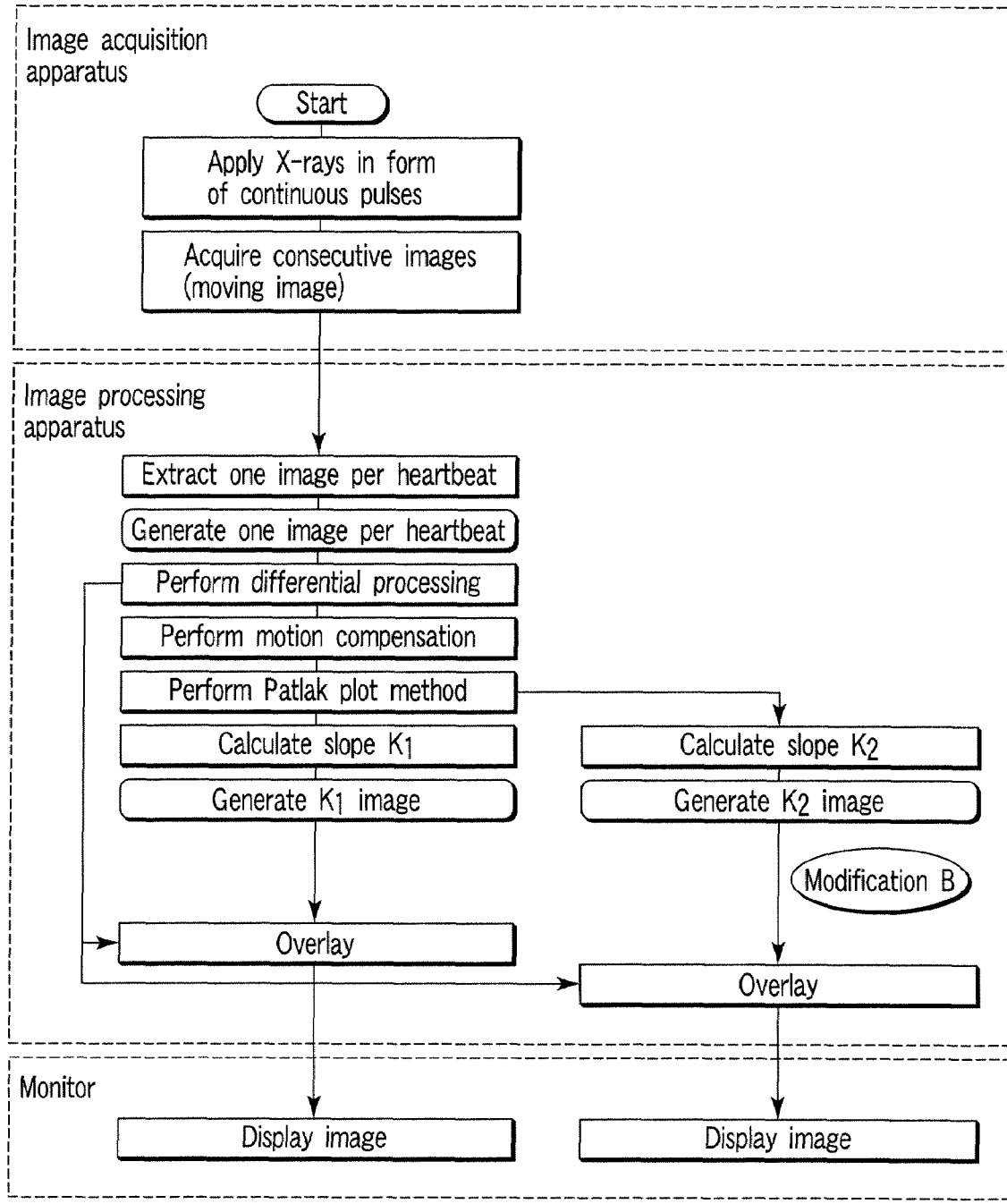
FIG. 24 is a flowchart showing another processing procedure in this embodiment.
Figure 25A:
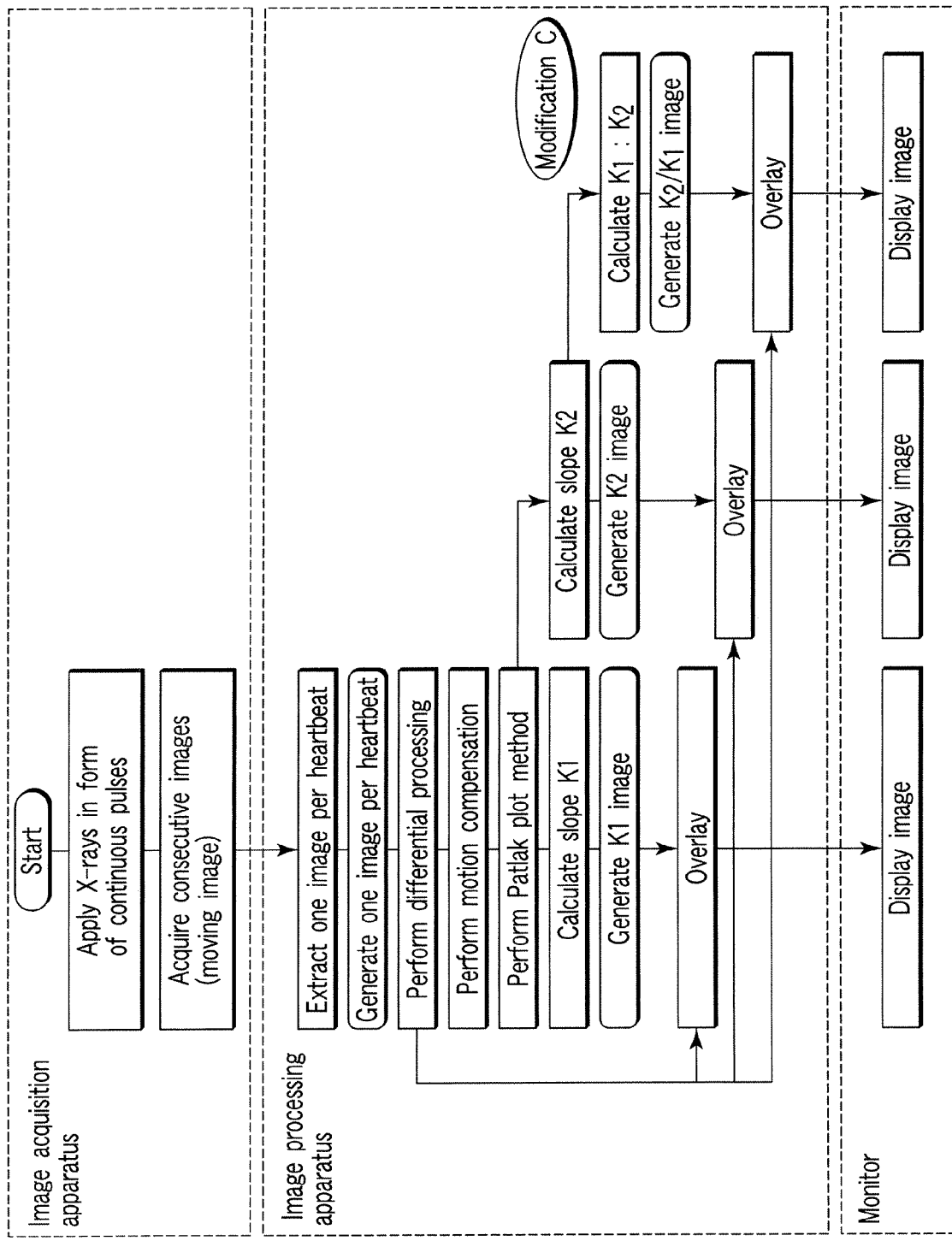
FIG. 25A is a flowchart showing another processing procedure in this embodiment.

The image processing unit 11 calculates the indexes $K_1$ and $K_2$ (FIG. 24). The image processing unit 11 calculates a ratio $K_2/K_1$ of the index $K_2$ to the index $K_1$ (FIG. 25A). The image processing unit 11 generates a $K_2/K_1$ ratio map.

Figure 25B:
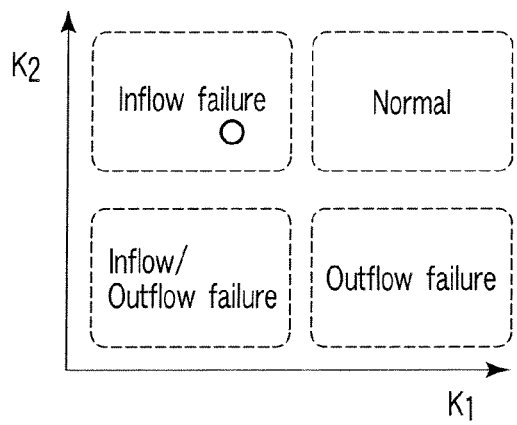
FIG. 25B is a view showing the distribution of two types of indexes in this embodiment.

As shown in FIG. 25B, the image processing unit 11 plots points corresponding to $K_1$ and $K_2$ for each local region with the abscissa and ordinate respectively representing $K_1$ and $K_2$. On the distribution, the respective local myocardial regions can be classified to four segments representing myocardial functions such as "normal", "inflow failure", "outflow failure", and "outflow/inflow failure". That is, local myocardial regions are classified to a combination of higher and lower distinctions with respect to a first threshold TH1 of the index $K_1$ and higher and lower distinctions with respect to a second threshold TH2 of the index $K_2$. This makes it possible to determine a myocardial function for each local region.

Figure 33:
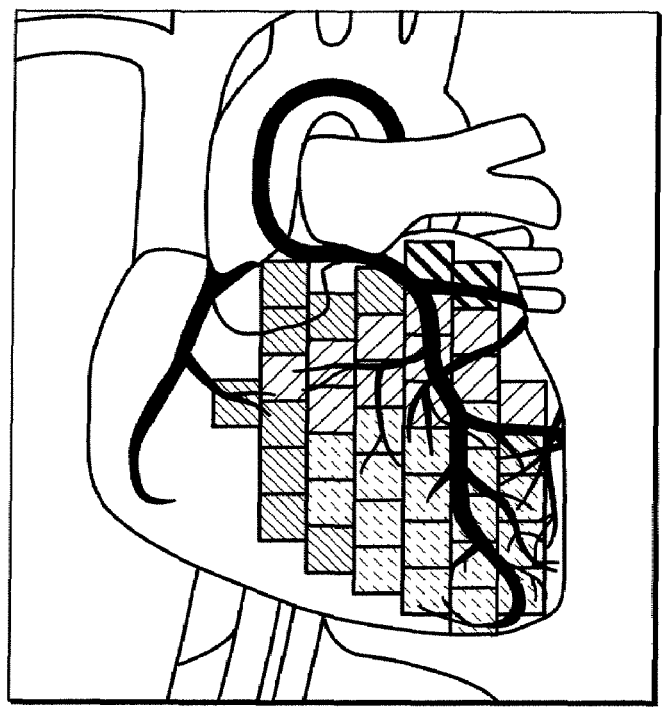
FIG. 33 is a view showing another myocardial function map in FIG. 32A.

In addition, as shown in FIG. 32B, the image processing unit 11 may assign four codes (1 to 4) to four segments and superimpose and display the codes on the original image upon assigning the codes to the respective local myocardial regions, as shown in FIG. 32A. Alternatively, as shown in FIG. 33, it suffices to discriminate the four segments by using different display forms, e.g., different luminances or hues and superimpose and display them on the original image. This display allows the operator to discriminate the states of myocardial failures and spatially grasp them.

Figure 29B:
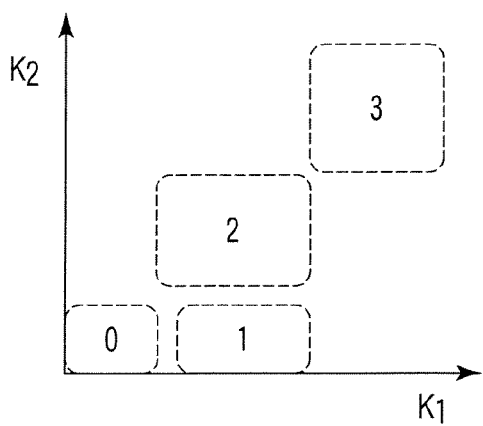
FIG. 29B is a view showing segments on an index distribution corresponding to the classification table in FIG. 28.

It also suffices to classify the segments as shown in FIGS. 28 and 29B.

Figure 26:
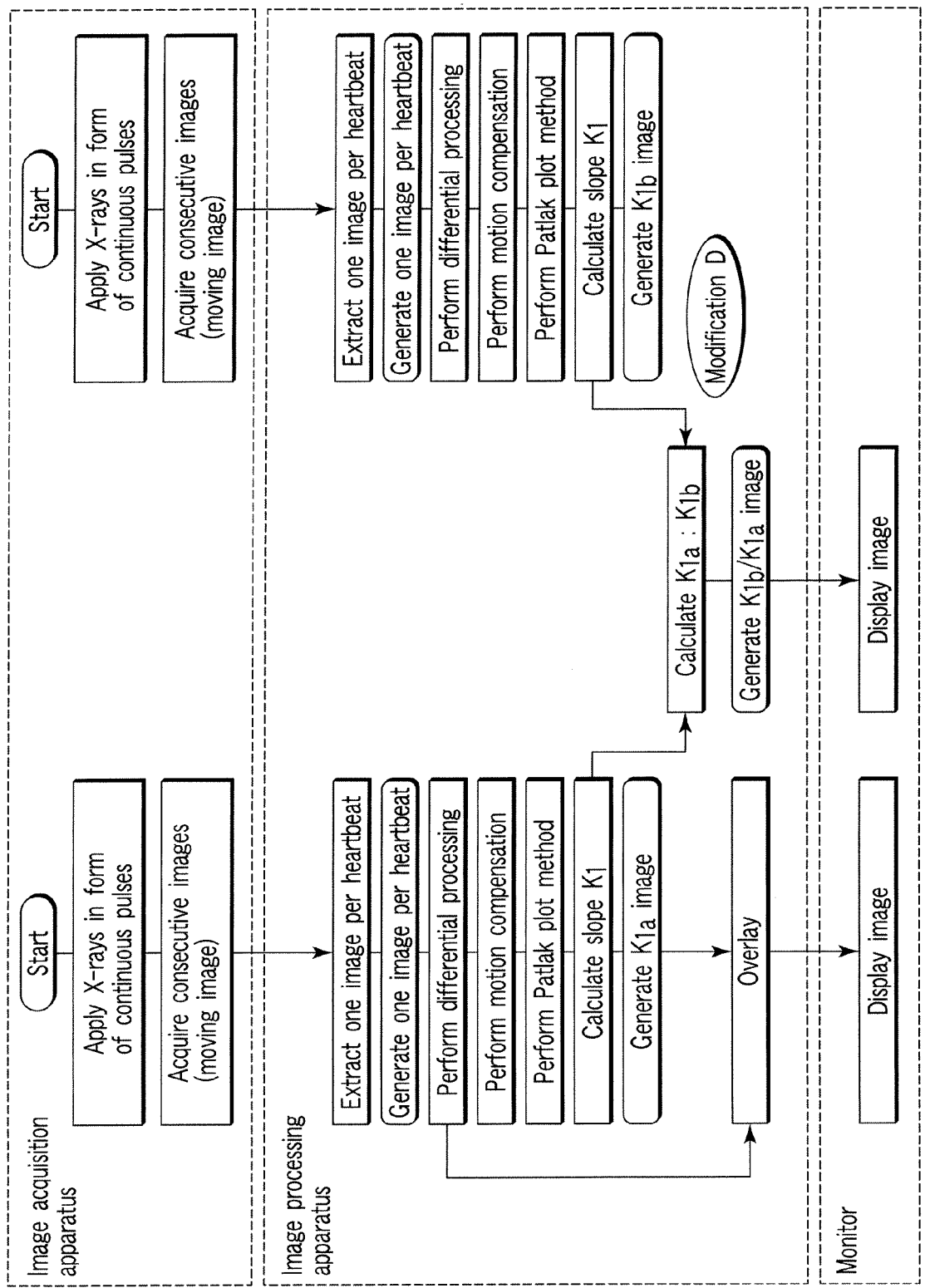
FIG. 26 is a flowchart showing still another processing procedure in this embodiment.

The image processing unit 11 also comprises a comparison analysis processing function (FIG. 26). For example, the image processing unit 11 calculates indexes $K_1$ at times A and B (C, D, E, . . . ) during the same operation and display them side by side. Alternatively, the image processing unit 11 may temporally switch and display the indexes. The image processing unit 11 calculates the ratio between $K_1$ at time A and $K_1$ at time B (C, D, E, . . . ) and displays the ratio in the form of an image. The image processing unit 11 superimposes and displays the original image on the color image of the ratio. For example, superimposing and displaying a color image of the ratio between indexes before and after a treatment on an original image can know which region of the cardiac muscle has achieved blood flow recovery owing to the treatment upon visualizing the region.

This embodiment described above has the following characteristics.

This embodiment differs from the perfusion calculation method using the contrast medium output from an X-ray CT apparatus in that image processing greatly differs depending on CT or X-rays, and processing unique to X-rays is required. Since X-ray images are moving images, the embodiment requires unique contrivances, more specifically, unique processing such as extraction of one image per heartbeat, background differential processing, motion compensation processing, processing in the thickness direction, and blood vessel ROI setting.

This embodiment differs from the known method of checking the slope of a time density curve based on X-rays in the idea itself described with reference to "theories 1 and 2". With regard to the index $K_1$, in the prior art, there is no idea of drawing a graph with the abscissa representing an inflow amount. This makes it necessary to perform different analysis processing and obtain different resultant images in the subsequent stages. The processing method is totally different from the processing of obtaining the slope of a time density curve.

The MBG (TMP) method in the reference (or in FIG. 28) assigns no meaning to any image numerical value itself. Obviously, this embodiment is higher in utility than the MBG method in terms that each image numerical value represents the velocity of inflow to the cardiac muscle. Since each image numerical value is normalized by an inflow amount, quantitativeness can be obtained even in a clinical case without being influenced by the amount of contrast medium to be injected.

Since this processing is not based on a visual check, quantitativeness is ensured. Since a prognosis can be predicted, it is possible to determine with reference to this value whether to terminate the intervention treatment. Since it is possible to compare the flow rates before and after processing (treatment), the operator can know how much the flow rate has increased, i.e., how much blood supply to the cardiac muscle has improved. Automating this processing makes it possible to easily use this technique even in a clinical case.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
   an X-ray generating unit which generates pulse X-rays;
   an X-ray detector which detects X-rays transmitted through a subject;
   an image generating unit which generates images based on an output from the X-ray detector; and
   a control unit which controls the X-ray generating unit to repeatedly generate the pulse X-rays in a radiography period and change a generation cycle of the pulse X-rays in the radiography period.

2. An apparatus according to claim 1, wherein the control unit causes the pulse X-rays to be generated at a constant cycle in a first interval in the radiography period and causes the pulse X-rays to be generated at an indefinite cycle in an ECG-gated mode in a second interval in the radiography period.

3. An apparatus according to claim 2, wherein the control unit switches between the first interval and the second interval with reference to a time point of a start of injection of a contrast medium or an end of injection of the contrast medium with respect to the subject.

4. An apparatus according to claim 3, wherein the control unit switches between the first interval and the second interval at a time point when a predetermined delay time has elapsed after a time point of the start of injection of the contrast medium or the end of injection of the contrast medium.

5. An apparatus according to claim 2, wherein the control unit switches between the first interval and the second interval on the basis of a density of the image.

6. An apparatus according to claim 2, wherein the first interval is set to one to five sec in advance, and the second interval is set to one to 60 sec in advance.

7. An apparatus according to claim 2, wherein the first interval is set to an arbitrary time length in advance, and the second interval is set to an arbitrary heart rate.

8. An apparatus according to claim 2, wherein the pulse X-rays are generated at 10 to 30 times/sec in the first interval, and are generated at one to five times/heartbeat in the second interval.

9. An apparatus according to claim 1, wherein the control unit causes the pulse X-rays to be generated at an indefinite cycle in an ECG-gated mode in a first interval in the radiography period, causes the pulse X-rays to be generated at a constant cycle in a second interval following the first interval in the radiography period, and causes the pulse X-rays to be generated at an indefinite cycle in the ECG-gated mode in a third interval following the second interval in the radiography period.

10. An apparatus according to claim 9, wherein the control unit switches the first interval to the second interval with reference to a time point of a start of injection of a contrast medium with respect to the subject, and switches the second interval to the third interval with reference to a time point of an end of injection of the contrast medium.

11. An apparatus according to claim 1, wherein the control unit causes the pulse X-rays to be generated at a first cycle in a first interval in the radiography period, and causes the pulse X-rays to be generated at a second cycle different from the first cycle in a second interval in the radiography period.

12. An apparatus according to claim 11, wherein the control unit switches between the first interval and the second interval with reference to a time point of a start of injection of a contrast medium or an end of injection of the contrast medium with respect to the subject.

13. An apparatus according to claim 1, wherein the control unit causes the pulse X-rays to be generated at a first cycle in a first interval in the radiography period, causes the pulse X-rays to be generated at a second cycle shorter than the first cycle in a second interval following the first interval in the radiography period, and causes the pulse X-rays to be generated at a third cycle longer than the second cycle in a third interval in the radiography period.

14. An apparatus according to claim 13, wherein the control unit causes the pulse X-rays to be generated at an indefinite cycle in an ECG-gated mode in a first interval in the radiography period, causes the pulse X-rays to be generated at a constant cycle in a second interval following the first interval in the radiography period, and causes the pulse X-rays to be generated at an indefinite cycle in the ECG-gated mode in a third interval in the radiography period.

15. An apparatus according to claim 1, wherein the control unit prolongs or shortens a generation cycle of the pulse X-rays at a time point designated by an operator in the radiography period.

16. An apparatus according to claim 1, wherein the control unit controls the X-ray detector to repeat X-ray detecting operation at a constant cycle over the first interval and the second interval.

17. An apparatus according to claim 2 or 9, further comprising a storage unit which stores data of the images separately for the first interval and the second interval.

18. An apparatus according to claim 17, further comprising a playback unit which plays back the images separately for the first interval and the second interval.

19. An image processing apparatus comprising:
    a storage unit which stores data of a plurality of images generated in an angiography sequence; and
    a computation unit which generates a reference time density curve concerning a reference region set in a blood supply region to a blood supplied region and a plurality of time density curves concerning a plurality of local regions set in the blood supplied region on the basis of the data of said plurality of images, and computes a plurality of indexes respectively representing correlations of said plurality of time density curves with respect to the reference time density curve.

20. An apparatus according to claim 19, wherein the angiography sequence is designed for a coronary artery, and the blood supplied region is cardiac muscle.

21. An apparatus according to claim 20, wherein the computation unit computes a correlation of the time density curve with respect to the reference time density curve in an inflow period of a contrast medium to the cardiac muscle as the index for said each local region.

22. An apparatus according to claim 20, wherein the computation unit computes a correlation of the time density curve with respect to the reference time density curve in an outflow period of a contrast medium from the cardiac muscle as the index for said each local region.

23. An apparatus according to claim 20, wherein the computation unit computes, for said each local region, a first index representing a correlation of the time density curve with respect to the reference time density curve in an inflow period of a contrast medium to the cardiac muscle, and a second index representing a correlation of the time density curve with respect to the reference time density curve in an outflow period of a contrast medium from the cardiac muscle.

24. An apparatus according to claim 23, wherein the computation unit computes a ratio between the first index and the second index for said each local region and generates a map of the ratios.

25. An apparatus according to claim 23, further comprising a display unit which superimposes and displays the map of the ratios on the image.

26. An apparatus according to claim 20, further comprising a display unit which displays the reference time density curve as a graph together with the time density curve.

27. An apparatus according to claim 23, wherein the computation unit classifies the local regions into a combination of higher and lower distinctions with respect to a first threshold of the first index and higher and lower distinctions with respect to a second threshold of the second index.

28. An apparatus according to claim 27, wherein the computation unit generates a map concerning the classified combination.

29. An apparatus according to claim 20, wherein the computation unit computes, as the index for said each local region, a correlation of the reference time density curve in an inflow period of a contrast medium to the cardiac muscle, which is acquired after a treatment, with respect to the reference time density curve in an inflow period of a contrast medium to the cardiac muscle, which is acquired before the treatment.

30. An apparatus according to claim 20, wherein the computation unit computes a comparison result on the index obtained from the data of the image acquired after a treatment with respect to the index obtained from the data of the image acquired before the treatment.

31. An apparatus according to claim 30, wherein the index is obtained from the data of the image in an inflow period of a contrast medium to the cardiac muscle.

32. An apparatus according to claim 30, wherein the index is obtained from the data of the image in an outflow period of a contrast medium to the cardiac muscle.

33. An apparatus according to claim 20, wherein the computation unit computes a comparison result on the index obtained from the data of the image acquired after administration of a drug with respect to the index obtained from the data of the image acquired before administration of the drug.

34. An apparatus according to claim 20, wherein the computation unit generates a map concerning the indexes.

35. An apparatus according to claim 34, further comprising a display unit which overlays and displays the map concerning the indexes on the image.

36. An apparatus according to claim 31, wherein the computation unit generates a map concerning the first index and a map concerning the second index.

37. An X-ray diagnostic apparatus comprising:
an X-ray generating unit which generates pulse X-rays;
an X-ray detector which detects X-rays transmitted through a subject;
an image generating unit which generates an image on the basis of an output from the X-ray detector;
a control unit which controls the X-ray generating unit to repeatedly generate the pulse X-rays in a radiography period and change a generation cycle of the pulse X-rays in the radiography period; and
a computation unit which generates a reference time density curve concerning a reference region set in a blood supply region to a blood supplied region and a plurality of time density curves concerning a plurality of local regions set in the blood supplied region on the basis of data of a plurality of images generated in an angiography sequence, and computes a plurality of indexes respectively representing correlations of said plurality of time density curves with respect to the reference time density curve.

* * * * *